(12) United States Patent
Goldfarb et al.

(10) Patent No.: US 9,808,144 B2
(45) Date of Patent: Nov. 7, 2017

(54) SWING PRISM ENDOSCOPE

(71) Applicant: Acclarent, Inc., Irvine, CA (US)

(72) Inventors: Eric Goldfarb, Belmont, CA (US);
Dominick L. Gatto, Fairfield, CT (US);
Thomas R. Jenkins, Alameda, CA (US); Scott J. Baron, Menlo Park, CA (US)

(73) Assignee: Acclarent, Inc., Irvine, CA (US)

( * ) Notice: Subject to any disclaimer, the term of this patent is extended or adjusted under 35 U.S.C. 154(b) by 0 days.

(21) Appl. No.: 15/069,231

(22) Filed: Mar. 14, 2016

(65) Prior Publication Data

US 2016/0256038 A1 Sep. 8, 2016

Related U.S. Application Data

(63) Continuation of application No. 13/465,757, filed on May 7, 2012, now abandoned, which is a
(Continued)

(51) Int. Cl.
*A61B 1/04* (2006.01)
*A61B 1/06* (2006.01)
(Continued)

(52) U.S. Cl.
CPC ...... *A61B 1/00183* (2013.01); *A61B 1/00039* (2013.01); *A61B 1/00066* (2013.01);
(Continued)

(58) Field of Classification Search
CPC ... A61B 1/00183; A61B 1/05; A61B 1/00181; A61B 1/00179; A61B 1/0052; A61B 1/00188
(Continued)

(56) References Cited

U.S. PATENT DOCUMENTS 3,804,081 A   4/1974   Kinoshita et al.
3,856,000 A   12/1974  Chikama
(Continued)

FOREIGN PATENT DOCUMENTS

DE   8810044   11/1988
EP   1166710   1/2002
(Continued)

OTHER PUBLICATIONS

Australian Patent Examination Report No. 1 dated Jun. 5, 2014 re Application No. 2009276931.
(Continued)

*Primary Examiner* — Anhtuan T. Nguyen
*Assistant Examiner* — William Chou
(74) *Attorney, Agent, or Firm* — Frost Brown Todd LLC

(57) ABSTRACT

A variable direction of view endoscope is positionable at desired locations within the ear, nose, throat, paranasal sinuses or cranium to accomplish visualization. A method of use includes introducing the variable direction of view endoscope into a nasal cavity with the endoscope adjusted to a first direction of view between about 0 degrees and about 15 degrees relative to a longitudinal axis of the endoscope. A therapeutic device is introduced into the nasal cavity and the endoscope is adjusted to a second direction of view directed toward the sinus opening or passageway. The method also includes advancing the therapeutic device into or through the sinus opening and viewing at least one of the sinus opening or passageway or the therapeutic device using the endoscope adjusted to the second direction of view.

7 Claims, 18 Drawing Sheets

Related U.S. Application Data continuation-in-part of application No. 13/464,180, filed on May 4, 2012, now abandoned, which is a continuation-in-part of application No. 12/502,101, filed on Jul. 13, 2009, now abandoned.

(60) Provisional application No. 61/084,949, filed on Jul. 30, 2008.

(51) Int. Cl.
  *A61B 1/00*   (2006.01)
  *A61B 1/12*   (2006.01)
  *A61B 17/24*   (2006.01)
  *A61M 29/02*   (2006.01)
  *A61B 1/233*   (2006.01)

(52) U.S. Cl.
  CPC .......... *A61B 1/00096* (2013.01); *A61B 1/126* (2013.01); *A61B 1/233* (2013.01); *A61B 17/24* (2013.01); *A61M 29/02* (2013.01)

(58) Field of Classification Search
  USPC ....... 600/109, 131, 133, 160, 167, 170, 171, 600/173
  See application file for complete search history.

(56) References Cited

U.S. PATENT DOCUMENTS

| | | | |
|---|---|---|---|
| 3,871,365 | A | 3/1975 | Chikama |
| 6,306,084 | B1 | 10/2001 | Pinczower |
| 6,500,115 | B2 | 12/2002 | Krattiger et al. |
| 6,560,013 | B1 | 5/2003 | Ramsbottom |
| 6,626,828 | B2 | 9/2003 | Dohi et al. |
| 6,648,817 | B2 | 11/2003 | Schara et al. |
| 6,817,976 | B2 | 11/2004 | Rovegno |
| 7,066,879 | B2 | 6/2006 | Fowler |
| 7,090,685 | B2 | 8/2006 | Kortenbach |
| 7,462,175 | B2 | 12/2008 | Chang et al. |
| 7,654,997 | B2 | 2/2010 | Makower et al. |
| 7,720,521 | B2 | 5/2010 | Chang et al. |
| 7,803,150 | B2 | 9/2010 | Chang et al. |
| 7,896,803 | B2 | 3/2011 | Schara et al. |
| 7,901,352 | B2 | 3/2011 | Minami |
| 8,485,968 | B2 * | 7/2013 | Weimer ............ A61B 1/00066 600/163 |
| 8,631,987 | B2 | 1/2014 | Shelton et al. |
| 8,852,087 | B2 | 10/2014 | Meyer et al. |
| 8,888,686 | B2 | 11/2014 | Drontle |
| 8,915,938 | B2 | 12/2014 | Keith |
| 8,961,398 | B2 | 2/2015 | Makower |
| 9,182,577 | B2 | 11/2015 | Hoeg |
| 9,278,199 | B2 | 3/2016 | Keith |
| 2005/0228230 | A1 * | 10/2005 | Schara ............... A61B 1/00045 600/171 |
| 2006/0004323 | A1 | 1/2006 | Chang et al. |
| 2006/0063973 | A1 | 3/2006 | Makower et al. |
| 2006/0069373 | A1 | 3/2006 | Schlinz et al. |
| 2006/0206006 | A1 * | 9/2006 | Schara ............... A61B 1/00177 600/173 |
| 2007/0167682 | A1 | 7/2007 | Goldfarb et al. |
| 2008/0103521 | A1 | 5/2008 | Makower |
| 2008/0167527 | A1 | 7/2008 | Slenker |
| 2008/0172033 | A1 | 7/2008 | Keith |
| 2008/0310181 | A1 | 12/2008 | Gurevich et al. |
| 2010/0030031 | A1 | 2/2010 | Goldfarb et al. |
| 2010/0047733 | A1 | 2/2010 | Nahlieli |
| 2013/0006055 | A1 | 1/2013 | Goldfarb et al. |
| 2013/0184532 | A1 | 7/2013 | Goldfarb et al. |
| 2015/0148610 | A1 | 5/2015 | Goldfarb et al. |

FOREIGN PATENT DOCUMENTS

| | | |
|---|---|---|
| JP | 07-327916 | 12/1995 |
| JP | 10-276976 | 10/1998 |
| JP | 2003-510119 | 3/2003 |
| JP | 2005-257734 | 9/2005 |
| JP | 2007-044183 | 2/2007 |

OTHER PUBLICATIONS

Canadian Office Action dated May 28, 2015 re Application No. 2,732,735.
Chinese First Office Action dated Dec. 5, 2012 re Application No. 200980130769.
Chinese First Search Report dated Nov. 19, 2012 re Application No. 200980130769.
International Search Report dated Dec. 16, 2009 for Application No. PCT/US2009/050800.
Japanese Notice of Reasons of Refusal dated May 21, 2013 re Application No. 2011-521178.
Japanese Notice of Reasons of Refusal dated Dec. 10, 2013 re Application No. 2011-521178.
Japanese Final Notice of Reasons of Refusal dated Dec. 10, 2013 re Application No. 2011-521178.
Korean Notice of Preliminary Rejection dated Aug. 20, 2015 re Application No. 10-2011-7004165.
Mexican Office Action dated Mar. 20, 2014 re Application No. MA/a/2011/001098.
Mexican Office Action dated Sep. 3, 2014 re Application No. MA/a/2011/001098.
U.S. Appl. No. 13/464,180, filed May 4, 2012.
U.S. Appl. No. 61/084,949, filed Jul. 30, 2008.
U.S. Appl. No. 61/511,304, filed Jul. 25, 2011.
Canadian Office Action dated May 12, 2016 for Application No. CA 2,732,735, 5 pages.
Chinese Second Office Action dated Jul. 22, 2013 for Application No. CN 200980130769.2, 10 pages.
International Preliminary Report on Patentability and Written Opinion dated Feb. 1, 2011 for Application No. PCT/US2009/050800, 8 pages.

* cited by examiner

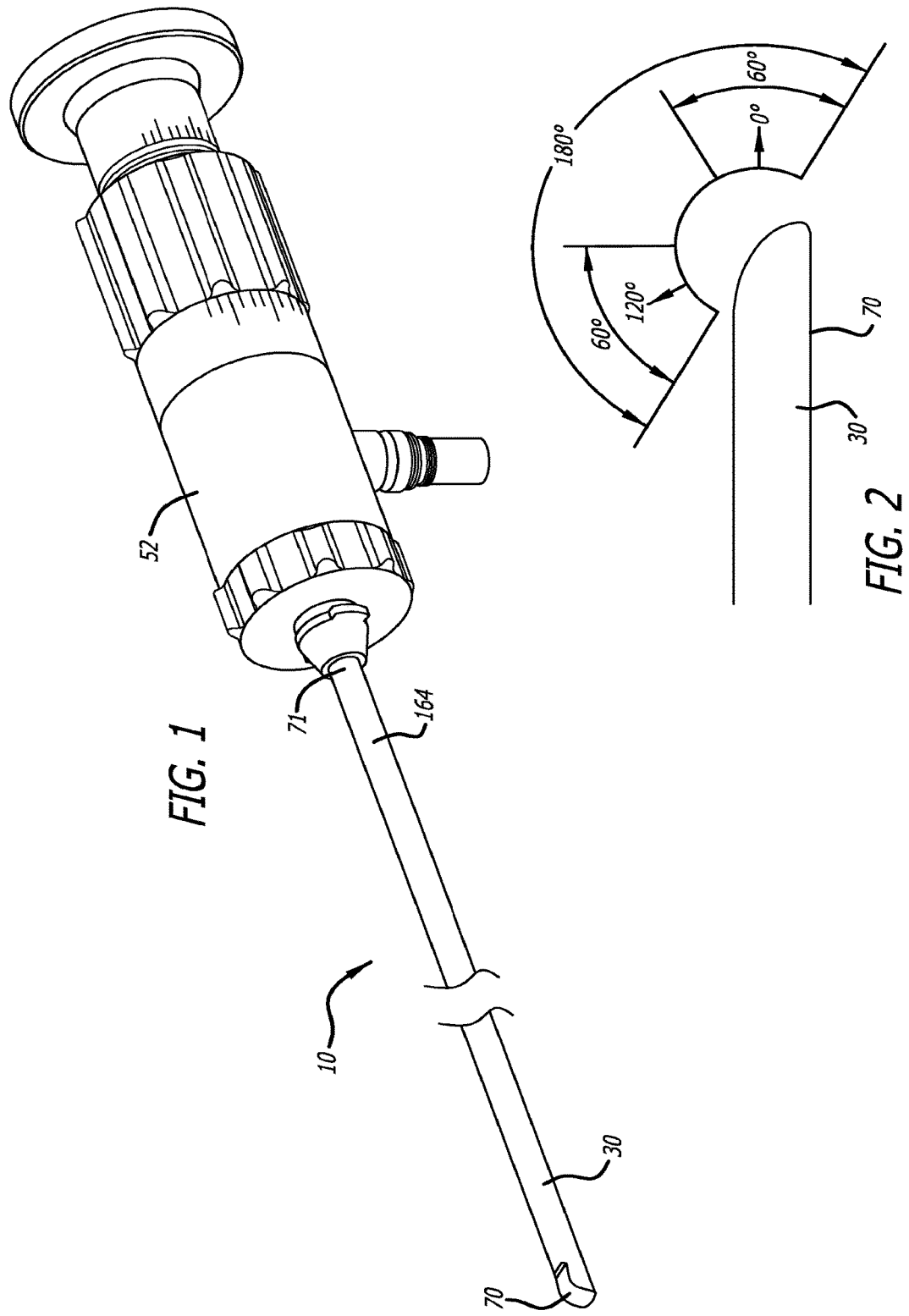

SWING PRISM ENDOSCOPE

CROSS-REFERENCES TO RELATED APPLICATIONS

This application is a continuation of application Ser. No. 13/465,757, filed May 7, 2012, published as U.S. Pub. No. 2013/0006055 on Jan. 3, 2013, which is a continuation-in-part of application Ser. No. 13/464,180, filed May 4, 2012, now abandoned, which is a continuation-in-part of application Ser. No. 12/502,101, filed Jul. 13, 2009, published as U.S. Pub. No. 2010/0030031 on Feb. 4, 2010, which claims the benefit of Provisional Application Ser. No. 61/084,949, filed Jul. 30, 2008, the contents of which are incorporated by reference.

FIELD OF THE INVENTION

The present invention relates generally to medical apparatus and methods and more particularly to devices and methods to facilitate endoscopic viewing within the ear, nose, throat, paranasal sinuses or cranium.

BACKGROUND

Functional endoscopic sinus surgery (FESS) is currently the most common type of surgery used to treat chronic sinusitis. In a typical FESS procedure, an endoscope is inserted into the nostril along with one or more surgical instruments. The surgical instruments are then used to cut tissue and/or bone, cauterize, suction, etc. In most FESS procedures, the natural ostium (e.g., opening) of at least one paranasal sinus is surgically enlarged to improve drainage from the sinus cavity. The endoscope provides a direct line-of-sight view whereby the surgeon is typically able to visualize some but not all anatomical structures within the surgical field. Under visualization through the endoscope, the surgeon may remove diseased or hypertrophic tissue or bone and may enlarge the ostia of the sinuses to restore normal drainage of the sinuses. FESS procedures can be effective in the treatment of sinusitis and for the removal of tumors, polyps and other aberrant growths from the nose.

The surgical instruments used in prior art FESS procedures have included applicators, chisels, curettes, elevators, forceps, gouges, hooks, knives, saws, mallets, morselizers, needle holders, osteotomes, ostium seekers, probes, punches, backbiters, rasps, retractors, rongeurs, scissors, snares, specula, suction cannulae and trocars. The majority of such instruments are of substantially rigid design.

In order to adequately view the operative field through the endoscope and/or to allow insertion and use of rigid instruments, many FESS procedures of the prior art have included the surgical removal or modification of normal anatomical structures. For example, in many prior art FESS procedures, a total uncinectomy (e.g., removal of the uncinate process) is performed at the beginning of the procedure to allow visualization and access of the maxilary sinus ostium and/or ethmoid bulla and to permit the subsequent insertion of the rigid surgical instruments. Indeed, in most traditional FESS procedures, if the uncinate process is allowed to remain, such can interfere with endoscopic visualization of the maxillary sinus ostium and ethmoid bulla, as well as subsequent dissection of deep structures using the available rigid instrumentation.

More recently, new devices, systems and methods have been devised to enable the performance of FESS procedures and other ENT surgeries with minimal or no removal or modification of normal anatomical structures. Such new methods include, but are not limited to, uncinate-sparing procedures using Balloon Sinuplasty™ tools and uncinate-sparing ethmoidectomy procedures using catheters, non-rigid instruments and advanced imaging techniques (Acclarent, Inc., Menlo Park, Calif.). Examples of these new devices, systems and methods are described in incorporated U.S. patent application Ser. No. 10/829,917, entitled Devices, Systems and Methods for Diagnosing and Treating Sinusitis and Other Disorders of the Ears, Nose and/or Throat; Ser. No. 10/944,270, entitled Apparatus and Methods for Dilating and Modifying Ostia of Paranasal Sinuses and Other Intranasal or Paranasal Structures; Ser. No. 11/116,118, entitled Methods and Devices for Performing Procedures Within the Ear, Nose, Throat and Paranasal Sinuses; and Ser. No. 11/150,847, entitled Devices, Systems and Methods Useable for Treating Sinusitis, each of which is hereby incorporated herein, in its entirety. Procedures using Balloon Sinuplasty™ tools, such as those described in the above-noted applications, for example, may be performed using various types of guidance, including but not limited to C-arm fluoroscopy, transnasal endoscopy, optical image guidance and/or electromagnetic image guidance.

In FESS and Balloon Sinuplasty™ procedures, the surgeon typically holds an endoscope with one hand while using the other hand to manipulate surgical instruments. Recognizing the desirability of integrating an endoscope with an operative device so that both could be moved with a single hand, application Ser. No. 11/193,020, entitled Methods and Apparatus for Treating Disorders of the Ear, Nose and Throat (hereby incorporated by reference) describes a number of transnasally insertable sinus guides coupled or integrated with endoscopes.

Currently available endoscopes used in ear, nose and throat procedures are generally rigid endoscopes that view in only one direction—i.e., either straight ahead or at a fixed angle. At the same time, the nasal/paranasal anatomy is one of many folded and curved structures made of bone covered with soft tissue, thus often making it very challenging to advance and view anatomy with a rigid unidirectional endoscope. For example, it may be quite challenging to advance an endoscope into the nose and around the uncinate process to view the ostium of the maxillary sinus. In fact, this is at least one reason why the uncinate process is removed in traditional FESS procedures. Although angled endoscopes are available, to view the anatomy as desired a surgeon may often need to use multiple different endoscopes during a procedure, switching between endoscopes as different views are desired. This can be quite awkward and cumbersome as well as expensive.

Therefore, there is a need for new devices and methodology to facilitate endoscopic viewing of anatomy, guidewires, catheters and/or other devices in intracranial procedures, such as ear, nose and throat procedures like paranasal sinus surgery. Ideally, such devices and methods would involve direct viewing of anatomy and surgical tools using an endoscope. Also ideally, such an endoscope would be easy to manipulate and use and would be compatible with a variety of surgical tools and systems. At least some of these objectives will be met by the embodiments of the present invention.

SUMMARY

Various embodiments are directed to a variable direction of view, swing prism endoscope for use in ear, nose, throat and possibly other intracranial procedures. Such an endoscope is useful when the axis of movement is at an angle with respect to the working or interventional site. The scope allows the user to view anatomy, such as a paranasal sinus ostium, without using/exchanging multiple endoscopes during a procedure or removing tissue as may be required in a traditional FESS procedure. Such a scope may also allow a physician to view anatomy and surgical tools without using fluoroscopy or image guidance systems, or at least with limited use of such systems, so that a procedure might be performed in a clinic or procedure room setting rather than in an operating room. Eliminating the use of fluoroscopy during a Balloon Sinuplasty™ or other ear, nose and throat procedure makes such a procedure more convenient for the physician, as a C-arm fluoroscope is not required in the operating room or procedure room. Eliminating or reducing the use of fluoroscopy may also be advantageous for physician and patient because they both receive less (or no) radiation dose.

One embodiment includes a method for advancing a therapeutic device into or through an opening or passageway into a paranasal sinus. The paranasal sinus opening may include a maxillary sinus ostium, at least one of a frontal sinus ostium or a frontal sinus outflow tract, a sphenoid sinus ostium, or a natural or man made opening of an ethmoid sinus. The method includes introducing a variable direction of view endoscope into a nasal cavity with the endoscope adjusted to a first direction of view between about 0 degrees and about 15 degrees relative to a longitudinal axis of the endoscope. A therapeutic device is introduced into the nasal cavity and the endoscope is adjusted to a second direction of view directed toward the sinus opening or passageway. The method also includes advancing the therapeutic device into or through the sinus opening and viewing at least one of the sinus opening or passageway or the therapeutic device using the endoscope adjusted to the second direction of view.

In one embodiment, the therapeutic device used in this procedure includes a balloon dilation catheter and a balloon of the catheter is dilated to expand the opening or passageway into the paranasal sinus. The method may also include introducing a guide catheter into the nasal cavity. Introduction of the guide catheter may occur before the direction of view of the endoscope is adjusted. However, the direction of view of the endoscope may be adjusted before the guide catheter is introduced.

The therapeutic device may include a flexible device. Further, the therapeutic device may be advanced through a lumen of the guide catheter into or through the paranasal sinus opening. A guidewire may also be advanced through the lumen of the guide catheter and into the paranasal sinus before advancing the balloon catheter over the guidewire and through the guide catheter to position a balloon of the catheter in the sinus opening. In one embodiment, the guidewire may be a lighted guidewire having an illuminating distal end, and the lighted guidewire is used for transilluminating the paranasal sinus while the illuminating distal end is located in the sinus.

In one embodiment of the method for treating a paranasal sinus, the therapeutic device includes an irrigation catheter, and the paranasal sinus is irrigated using the irrigation catheter when at least one aperture of the irrigation catheter is located within the sinus. The therapeutic device may also include a drug delivery reservoir that is implanted in at least one of the sinus or the opening or passageway into the sinus.

Further, during the procedure, the endoscope may be adjusted to the first direction of view or to a third direction of view to view at least one of the therapeutic device or anatomy of the nasal cavity.

In another embodiment, the endoscope includes a swing prism endoscope. In this embodiment, adjusting the direction of view includes rotating a prism of the endoscope.

Another embodiment includes a method for viewing anatomy in a head of a human or animal subject by introducing a variable degree of view endoscope into the subject's head with the endoscope adjusted to a first degree of view. Also, the anatomy in the head is viewed using the endoscope with the first degree of view, and a first portion of a handle of the endoscope is rotated about a longitudinal axis of the endoscope to adjust the endoscope to a second degree of view. The first portion of the handle rotates relative to a shaft of the endoscope. Also, the anatomy in the head is viewed using the endoscope with the second degree of view. The method may include rotating a second portion of the handle about the longitudinal axis to rotate the shaft of the endoscope without rotating the rest of the handle. Also, rotating the first portion of the handle adjusts the endoscope to the first degree of view or to a third degree of view.

In one embodiment, the step of introducing the endoscope includes passing the endoscope into a nasal cavity. Once the endoscope has been introduced into the nasal cavity, the viewed anatomy may consist of the nasal cavity anatomy, an opening or passageway into a paranasal sinus ostium, a paranasal sinus, a Eustachian tube opening, an oral cavity, a nasopharynx, a throat, a larynx, and a trachea.

A physician or user may view a direction of view indicator on the endoscope indicating the direction of view in which the endoscope is pointing. The user may also view at least one medical or surgical device introduced into the subject's head with the endoscope.

One embodiment of a variable direction of view endoscope configured to pass into a head of a human or animal subject is also disclosed. The endoscope includes an elongate shaft having a proximal end, a distal end, and an outer diameter of no more than approximately 5 mm. A viewing window is disposed along the shaft at or near the endoscope's distal end, and a pivotable prism is disposed in the shaft near the distal end to change a direction of view of the endoscope. The viewing window extends from the distal end of the shaft proximally along one side of the shaft. There may also be a handle coupled with the proximal end of the elongate shaft. The handle includes a first rotating dial for adjusting the viewing angle of the endoscope by pivoting the prism, and the first rotating dial rotates about a longitudinal axis of the shaft. The handle may further include a second rotating dial for rotating the shaft of the endoscope without rotating the rest of the handle. In certain embodiments, the first and second dials are sealed to allow the endoscope to be sterilized in an autoclave without damaging the endoscope.

Also, the endoscope may include a self-focusing lens disposed in the shaft, configured to automatically focus the view acquired through the viewing window as the prism pivots.

A field of view of the endoscope is between approximately 60 degrees and approximately 70 degrees or from about 5 degrees to about 100 degrees. Also, a direction of view of the endoscope ranges from between about 0 degrees to about 120 degrees. In use, the endoscope is compatible with 300 Watt Xenon light sources. Also, the endoscope may include a handle attachment attached to the handle for facilitating holding the handle.

Further aspects, elements and advantages of the present invention will be described in further detail below in reference to the attached drawing figures. Although the various embodiments will typically be described in the context of paranasal sinus surgical procedures, in many embodiments the devices, systems and method described herein may be used in other ear, nose and throat procedures and/or in other intracranial procedures.

BRIEF DESCRIPTION OF THE DRAWINGS

FIG. 1 depicts a perspective view of a swing prism endoscope according to one embodiment of the present invention;

FIG. 2 depicts a side view, depicting viewing ranges of an endoscope equipped with a swing prism, according to one embodiment of the present invention;

DETAILED DESCRIPTION

Figure 3:
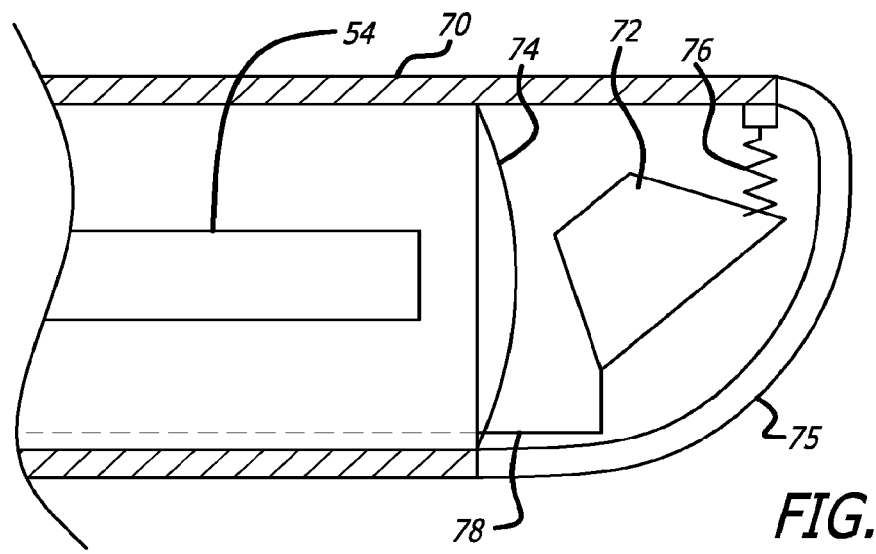
FIG. 3 depicts a cross-sectional view of a distal end of a swing prism endoscope, according to one embodiment of the present invention.

In the following description, where a range of values is provided, each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, the preferred methods and materials are now described. All publications mentioned herein are incorporated herein by reference to disclose and describe the methods and/or materials in connection with which the publications are cited.

As used herein and in the appended claims, the singular forms "a", "an", and "the" include plural referents unless the context clearly dictates otherwise. Thus, for example, reference to "a channel" includes a plurality of such channels and reference to "the endoscope" includes reference to one or more endoscopes and equivalents thereof, and so forth.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

The following detailed description, the accompanying drawings and the above-set-forth Brief Description of the Drawings are intended to describe some, but not necessarily all, examples or embodiments of the disclosure. The contents of this detailed description do not limit the scope of the disclosure in any way.

FIG. 1 shows a variable degree of view endoscope 10 according to one embodiment. The endoscope 10 may include an elongate shaft 30 with a distal end 70 and a proximal end 71, the latter being attached to a proximal body member or handle 52 that can be adapted to engage and attach to the adjustable scope/lock extension, and a swing prism (not shown, but described in relation to FIG. 3 et seq. below) for adjusting the viewing angle of the endoscope 10. The shaft 30 may house an image fiber bundle or optic fibers 54 that extends coaxially through its center, with light transmitting fibers 56 disposed about the periphery. In one embodiment, the shaft 30 may be a braided polyimide sheathing that has a maximum outer diameter of 0.0375 inches and a length of two feet. Preferably, the image fiber bundle is made up of 10,000 thin image fibers, and the light transmitting fibers are illumination fibers with a diameter of between about 0.008 and 0.020 inches, with a minimum lux of about 10,000. In another embodiment, the endoscope 10 may use rod lens technology instead of using image fiber bundles.

Referring now to FIG. 2, the distal end 70 of the endoscope shaft 30 is shown with angular measurements according to one embodiment. In describing FIG. 2, "field of view" means the angular width/height viewed at any one time via the endoscope, "direction of view" means the direction in which the center of view is pointing at any one time (also can be called the "degree of view" as in "variable degree of view endoscope") and "total range of view" means the total angular distance across which the endoscope can view when the swing prism is moved from one extreme direction of view to the opposite extreme direction of view. The angles referred to are in relation to the longitudinal axis of the endoscope shaft 30, which is the zero angle.

In some embodiments, for example, the endoscope 10 may have a range of directions of view from about −5° to about 150° and more likely from about 0° to about 120° or from about 5° to about 100°. In some embodiments, the endoscope may have a field of view from about 50° to about 100° or more likely from about 60° to about 70°. From the ranges of the directions of view and the fields of view, the total ranges of view may be determined. For example, in one embodiment the endoscope 10 may have directions of view ranging from about 5° to about 100° and may have a field of view of about 60°. In this embodiment, the total range of view would be from about −25° to about 130°. If the ranges of directions of view were instead from about 0° to about 120° and the field of view were about 60°, then the total range of view would be from about −30° to about 150°. In various embodiments, the endoscope 10 may have any of a number of different combinations and ranges of directions of view, fields of view and total ranges of view.

Figure 4:
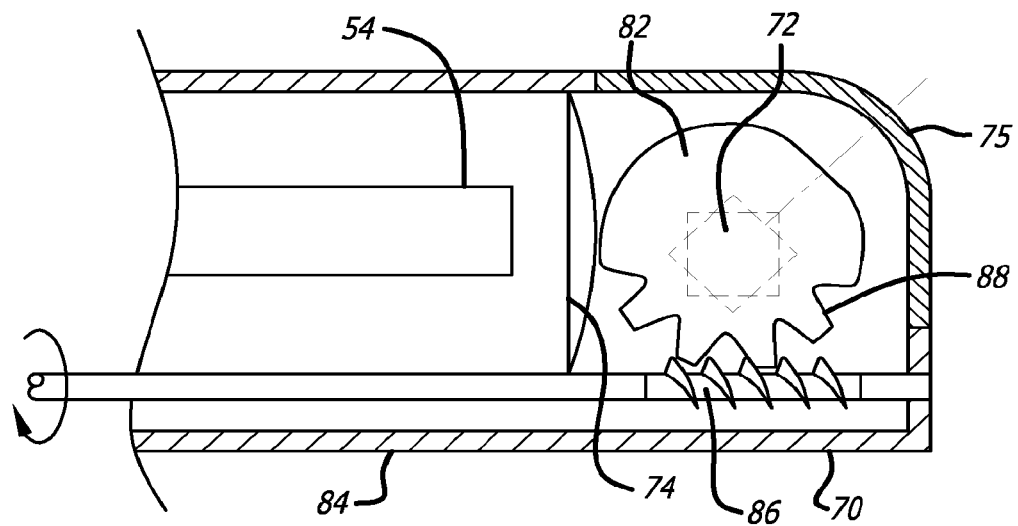
FIG. 4 depicts a cross-sectional view of a distal end of a swing prism endoscope, according to one embodiment of the present invention.
Figure 5:
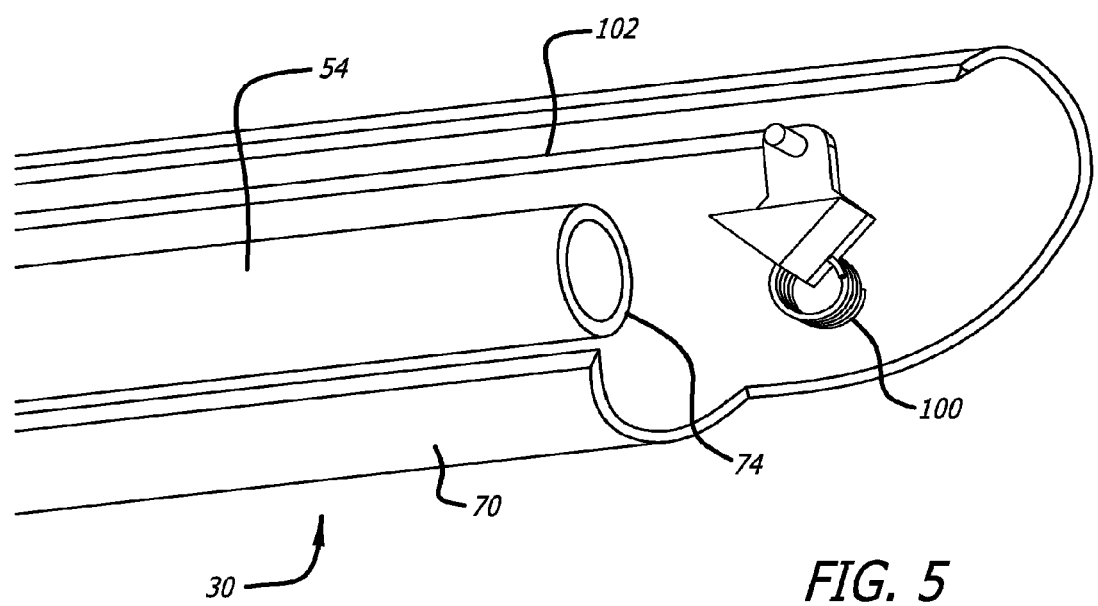
FIG. 5 is a cross-sectional view of a distal end of a swing prism endoscope, according to yet another embodiment of the present invention.

Referring now to FIGS. 3-5, various configurations distal portions 70 of the variable degree of view endoscope 10 are shown, each having different configurations of a swing prism 72 and/or mechanisms for mounting a swing prism 72. In a first approach, the swing prism 72 is mounted for rotation between a biasing spring 76 and an actuator 78. Here, the actuator 78 can come in the form of a wire which extends from the distal portion 70 of the endoscope 10 to a proximal portion which is conveniently accessible and manipulatable by an operator. In this regard, the actuator can be attached to a sliding member or configured to be taken up by a rotating dial (not shown). As so configured, images can be captured and received through a window 75 and transmitted through the swing prism 72 and self-focusing lens 74 to the image fiber bundle 54. The swing prism 72 provides the desired seventy degree field of view throughout a viewing range of zero degrees to ninety five degrees by manipulating the actuator 78.

In another approach shown in FIG. 4, the swing prism 72 can be mounted in a housing 82 placed in operative association with a rotatable shaft 84 which extends proximally to an operator. A distal portion of the shaft 84 is provided with threaded structure 86 arranged to engage teeth 88 formed on the housing 82. Rotating the shaft accomplishes positioning the swing prism 72 as desired. Again, these components can be arranged to provide a one hundred sixty five degree range of viewing.

In an approach shown in FIG. 5, the swing prism 72 is mounted for rotation between a torsion spring 100 and a pull wire 102. The torsion spring can be any spring, such as an extension spring, leaf spring, or the like. Here, the pull wire 102 may extend from the distal portion 70 of the endoscope shaft 30 to a proximal portion which is conveniently accessible and manipulatable by an operator. In this regard, the pull wire can be attached to a sliding member or configured to be taken up by a rotating dial. Images can be captured and received through the window (not shown) and transmitted through the swing prism 72 and self-focusing lens 74 to the image fiber bundle 54. In this embodiment, there is always tension on swing prism between the torsion spring and pull wire, so there is no lag or buckling in the pull wire during operation. Further, use of the pull wire and torsion spring to move the swing prism allows the diameter of the endoscope to be smaller.

The images collected by the image fiber bundle 54 can be transmitted to a monitor (described below) to thereby provide the operator with visual data concerning the particular interventional procedure being performed. In one embodiment, the endoscope 10 be compatible with a 300 Watt Xenon source and be configured with a universal light guide connector, thus making the assembly useable with conventionally available devices. In one embodiment, the endoscope shaft 30 may have an outer diameter of approximately 4 mm and a working length of about 175 mm. Moreover, the endoscope shaft 30 is preferably provided with rounded surfaces thus making the assembly atraumatic in use. It has also been found useful to construct the endoscope 10 in a manner and embodying material which permit the endoscope 10 to be sterilized using an autoclave.

In certain approaches, it may be useful to configure the endoscope 10 with indicia indicating the direction of view of the swing prism and/or a rotational position of the endoscope 10. Thus, a proximal portion of the actuator 78 of FIG. 3, for example, can be coupled with a dial which includes markings indicative of the angle of the swing prism 72. Similarly, a proximal end of the shaft 84 of FIG. 4 can be attached to a dial including indicia providing information relative to the angle of the swing prism 72. Moreover, the external surface of the endoscope 10 can include marking indicators rotational positioning of the overall assembly.

The swing prism endoscope 10 may be freely advanced within anatomy along with a sinus guide in order to facilitate endoscopic viewing of the desired anatomical structures and/or to view, guide and/or verify the positioning of the sinus guide device or a working device that has been inserted through the sinus guide. The ability to advance the tip of the endoscope 10 within anatomy to view the end of the sinus guide allows the devices to be positioned closer to anatomy or to reach spaces in the paranasal sinuses that the devices cannot travel due to size constraints.

Figure 6:
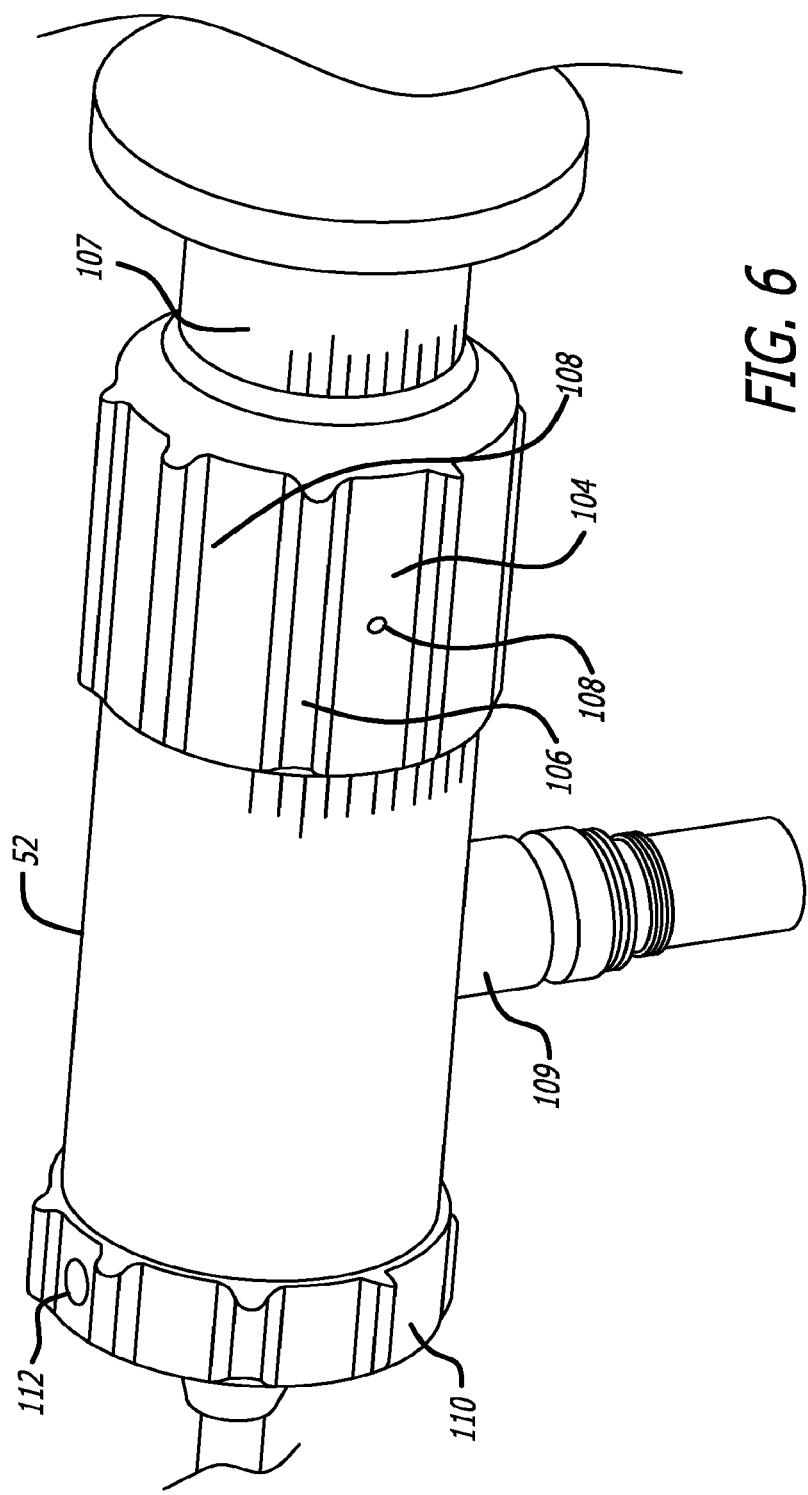
FIG. 6 depicts a side view of a proximal body member or handle of a swing prism endoscope equipped with turning dials to control the rotation of the endoscope shaft and rotation of the swing prism.

As discussed above with reference to FIGS. 3 through 5, the rotation of the swing prism may be controlled by a dial. As shown in FIG. 6, a proximal dial 104 is disposed on the handle 52 of the endoscope 10 for controlling the rotation of the swing prism. The proximal dial 104 has a circular configuration and includes ridges 106 that provide leverage for turning the proximal dial or dial to a desired position. Further, the ridges provide a tactile feel for the dial location and grooves 108 between the ridges provide an area for the user's fingers to rest. In one embodiment, there are eight ridges evenly placed around the proximal dial 104, however, there may be fewer or more ridges placed around the dial. The height of the ridges is approximately 0.05 inches, and can be increased or decreased depending on user preferences. Also, the spacing between each ridge is approximately 0.228 inches, and can be increased or decreased depending on the number of ridges disposed on the dial and the width of the ridges.

Still referring to FIG. 6, the handle 52 of the endoscope may include indicia 107 adjacent the proximal dial 104 to provide information relative to the angle of the swing prism 72. In this embodiment, there is also a marker 108 on the proximal dial itself indicating the relative angle of the swing prism 72. As shown, the indicia 107 adjacent the proximal dial indicate the relative angle of the swing prism 72 anywhere from 0 degrees to 180 degrees.

In one embodiment, a distal dial or shaft dial 110 is disposed on the handle 52 of the endoscope as shown in FIG. 6, and the shaft dial 110 controls rotation of the endoscope shaft 30. A marker 112 is shown on the shaft dial 110 to indicate the relative position of the endoscope shaft 30. More particularly, the marker 112 on the shaft dial indicates the relative position of the window 75 (see FIG. 3) at the distal portion 70 of the endoscope 10. As shown in FIG. 6, since the marker 112 is on the top side of the endoscope, the window 75 is also pointing towards the top side of the endoscope 10, allowing the endoscope 10 to view the surroundings in the same general direction. Rotating the shaft dial 110 allows the endoscope to view its surroundings in a full three-hundred and sixty degrees of rotation. Having a rotating shaft dial 110 that rotates the endoscope shaft 30 without rotating the entire handle 52 may be advantageous because it allows for rotation of the endoscope shaft 30 without rotating the light post 109.

Figure 7:
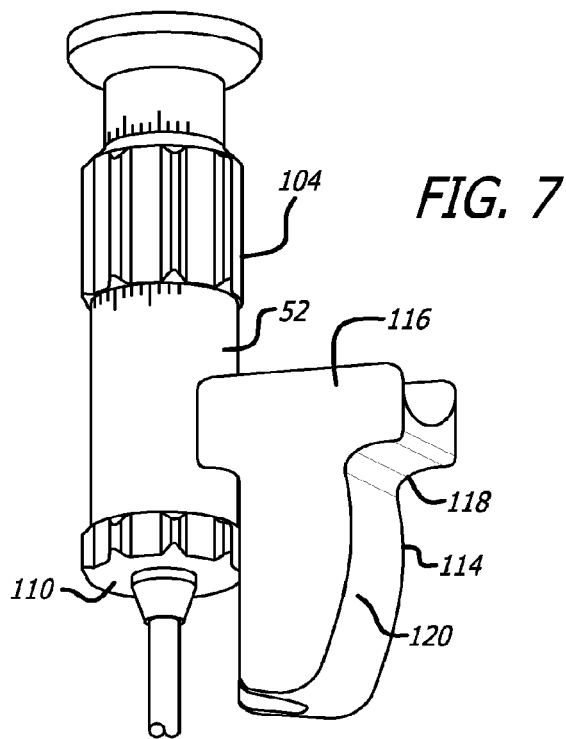
FIGS. 7-9 depict three different embodiments of a handle that can be attached to the handle of the swing prism endoscope.

FIG. 7 shows a handle attachment 114 attached to the handle 52 of the endoscope 10. The handle attachment 114 facilitates turning the dials 104 and 110 while the user is holding the endoscope 10. The handle attachment 114 is affixed to the handle 52 and/or may be snap fit onto the light post 109 stemming from the handle 52. A light post portion 116 of the handle attachment 114 snaps onto the light post 109 and shields the user from the heat radiating from the light post 109. When holding the handle attachment 114 and endoscope 10, the crook between the user's thumb and extended index finger is positioned at the curve 118 under the light post portion 116 of the handle while the palm of the user's hand rests on the body 120 of the handle attachment 114. The handle attachment 114 may provide the user with comfort and balance while holding the endoscope and may also provide additional torque to turn the dials 104 and 110. Holding the endoscope 10 with the handle attachment 114 allows the user to turn the proximal dial 104 with the thumb and index fingers, and the distal dial 110 can be accessed with the ring or pinkie finger.

Figure 8:
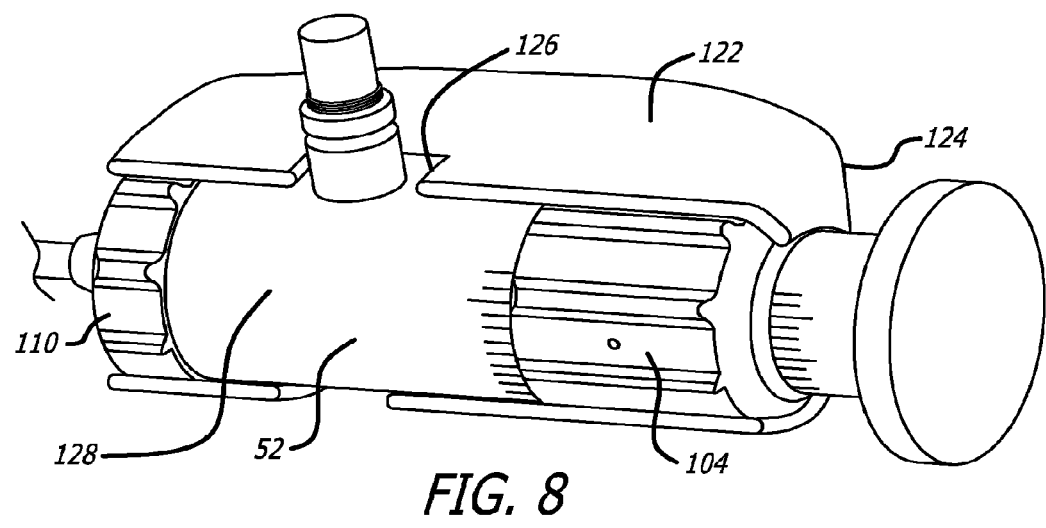

Another embodiment of a wrap-around handle attachment 122 that is snap-fit onto the handle 52 of the endoscope is shown in FIG. 8. The wrap-around handle attachment 122 allows the user to grip the endoscope tightly without impinging the rotation of the dials 104 and 110. A handle attachment back 124 is designed to be relatively long and rounded to fit a variety of positions within the palm of the user. With a light post cut out 126, the handle attachment 122 can be moved or positioned around the handle 52 about two hundred and seventy degrees to facilitate a variety of holds by the user. The handle attachment 122 includes an opening 128 that allows the handle attachment 122 to more than half-way overlap the dials and handle 52 of the endoscope 10 while still allowing access to the dials 104 and 110.

Figure 9:
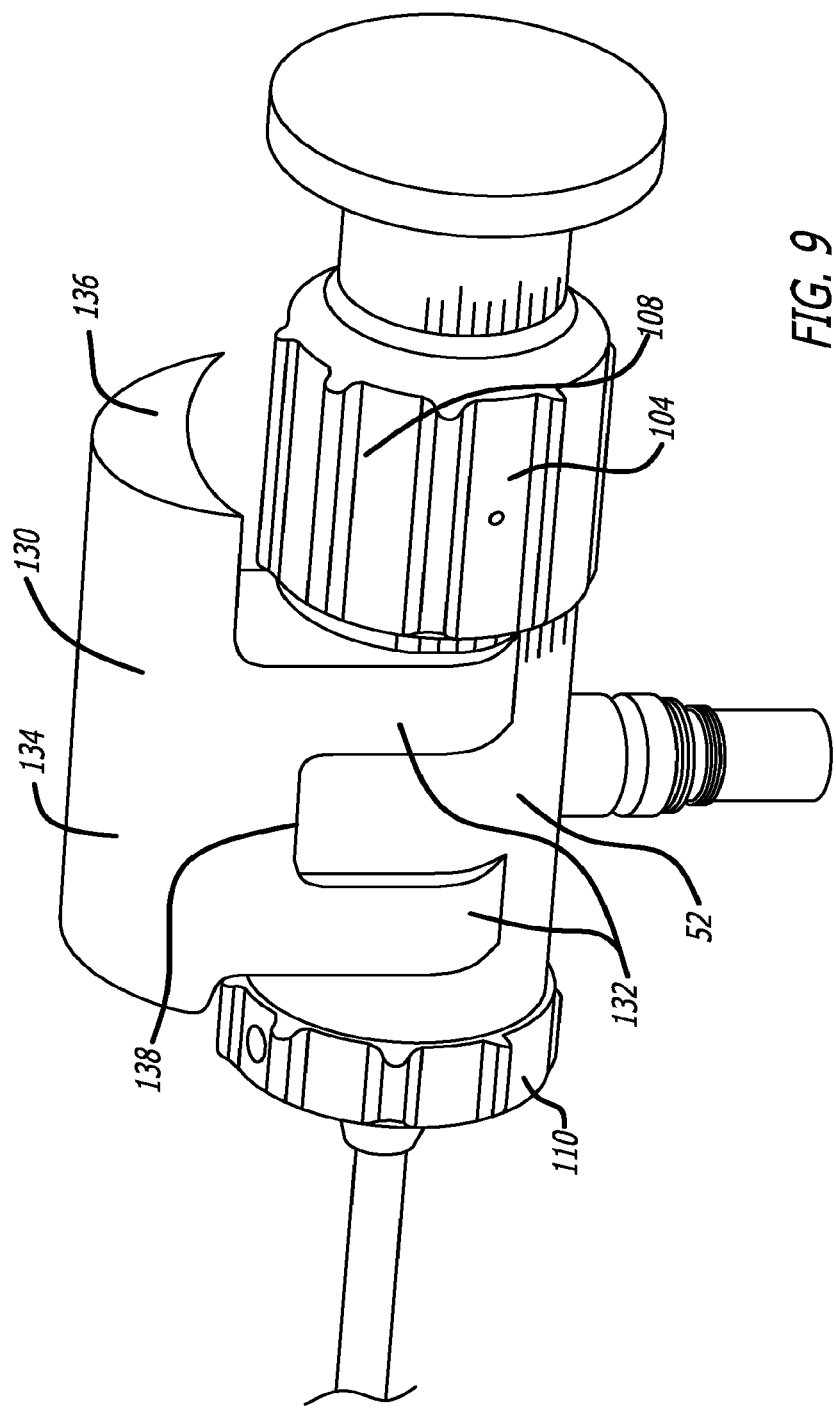

Yet another embodiment of a handle attachment 130, including legs 132 that snap-fit onto the handle 52 of the endoscope 10, is shown in FIG. 9. Handle attachment 130 includes a back 134 that fits against the user's palm and a dial cover 136 that extends over the proximal dial 104. A light post slot 138 can also be seen in FIG. 9 to accommodate the light post 109. The user is allowed to freely engage the dials 104 and 110 with his fingers when holding the endoscope 10 with the handle 130.

The optical fibers 54 of the endoscope 10 may be enclosed in a sealed chamber to allow the endoscope to be autoclaved.

Figure 10:
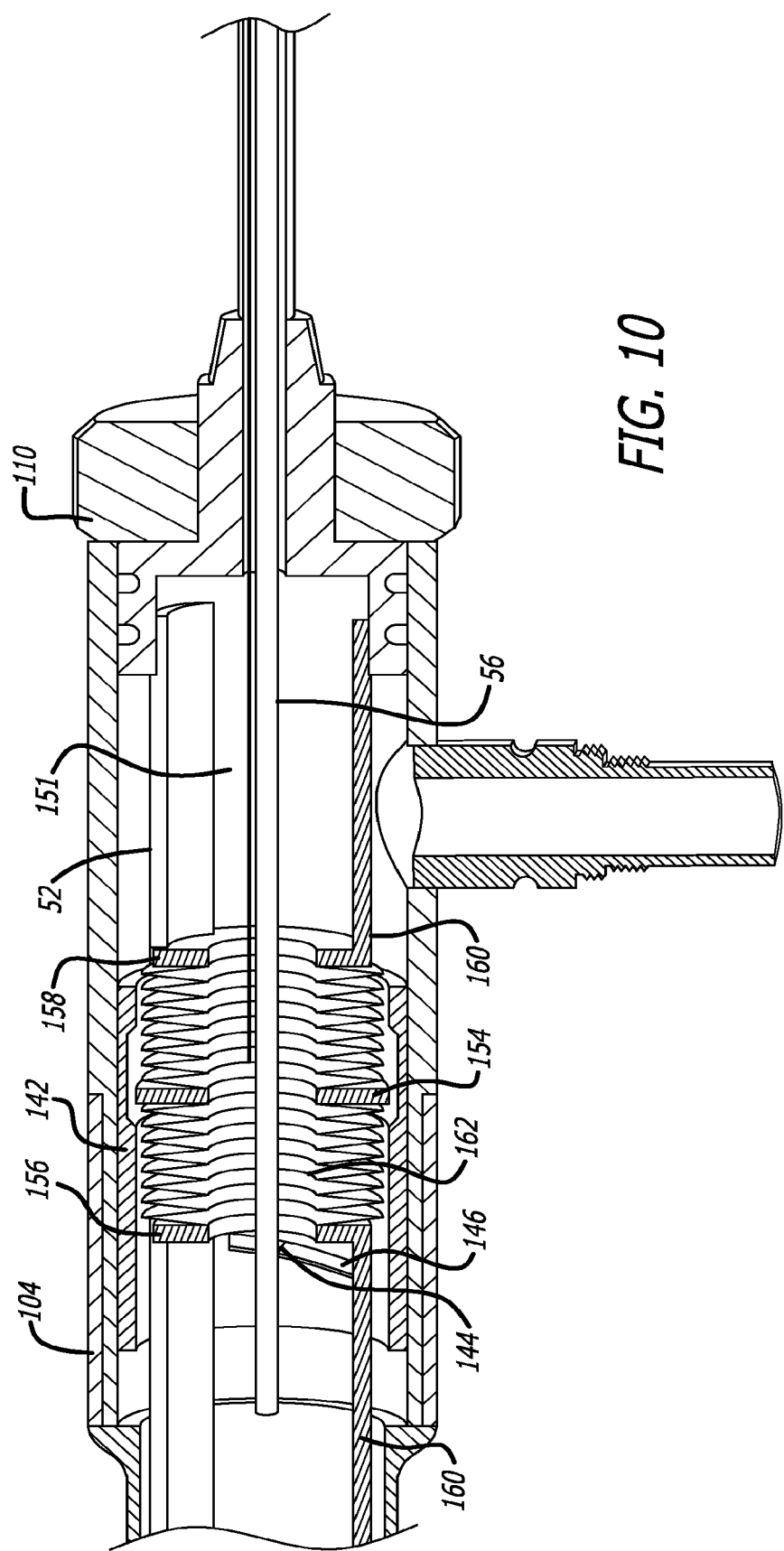
FIG. 10 depicts a cross-sectional view of the handle of a swing prism endoscope showing a sealed chamber and a driving mechanism using bellows to control the rotation of the swing prism.

In another embodiment shown in FIG. 10, a middle bellow joint 154 is attached to the housing 142 and is controlled in longitudinal motion by the proximal dial 104 which drives a screw mechanism. The pin 144 attached to the proximal dial extends into the handle 52 and through the curved slot disposed in the housing 142. There is also a proximal bellow joint 156 and a distal bellow joint 158 that are fixed within the endoscope on an inner shield 160, and there are flexible bellows 162 that are disposed between the bellow joints 154, 156, and 158. As the proximal dial 104 is turned, the pin moves along the curved slot and moves the housing 142 in a proximal or distal direction along the longitudinal axis of the endoscope and moves the middle bellow joint. As the middle bellow joint moves forwards and backwards, it drives the swing prism by moving the push/pull mechanism 152 that is attached to the middle bellow joint. The inner shield 160 creates the sealed chamber 151 for the optical fibers 54. The push/pull mechanism may be an actuator, pull wire, bar, hypotube, or the like, that is attached to the swing prism. In this embodiment, the bellow joints can easily transmit torque for rotation of a hypotube or rotatable shaft that can be attached to the middle bellow joint 154.

In one embodiment, the endoscope 10 is a re-usable instrument. Conventionally, endoscopes are processed between uses via steris, autoclave or other known processes. The time required to process the endoscope can be significant, resulting in delays between cases or the need to purchase multiple endoscopes for procedures occurring one after the other. One embodiment includes a disposable sterile sleeve 164 (see FIG. 1) that is used with the endoscope 10. The sterile sleeve is low-profile and optically clear at the distal tip to allow viewing with the prism. The sterile sleeve spans the full length of the endoscope that is inserted into the patient for the procedure so that there is no direct contact between the patient and the endoscope. Also, the sterile sleeve may cover the proximal end of the endoscope and camera so there is no direct contact between the user and the endoscope. Once a procedure is complete, the user simply removes and discards the sterile sleeve and then inserts a new sterile sleeve over the endoscope for the next case. Using the sterile sleeve may eliminate the need to process the endoscope between cases or in the office environment.

During case procedures, endoscopes have the tendency to lose visual clarity because of the debris, blood, and/or mucus adhering to the distal tip of the endoscope. Conventionally, surgeons or users remove the endoscope from the patient frequently to clean the distal tip of the endoscope. Alternatively, some surgeons use scope washing systems having an open sheath over the endoscope shaft to deliver fluid and/or vacuum to enable in situ cleaning. Each washing sheath is specifically designed for the endoscope geometry, and because endoscope distal tip geometries vary by viewing angles, there are also multiple cleaning sheaths that must be correspondingly used. Therefore, when a user wants to change the scope viewing angle during a procedure, the washing sheath must also be changed. In one embodiment described below, a washing system and sheath is used with the endoscope 10. As described above, the geometry of the endoscope 10 does not change when the direction of the desired view changes, and therefore, a single fixed sheath may be used with the swing prism endoscope described herein.

Figure 11:
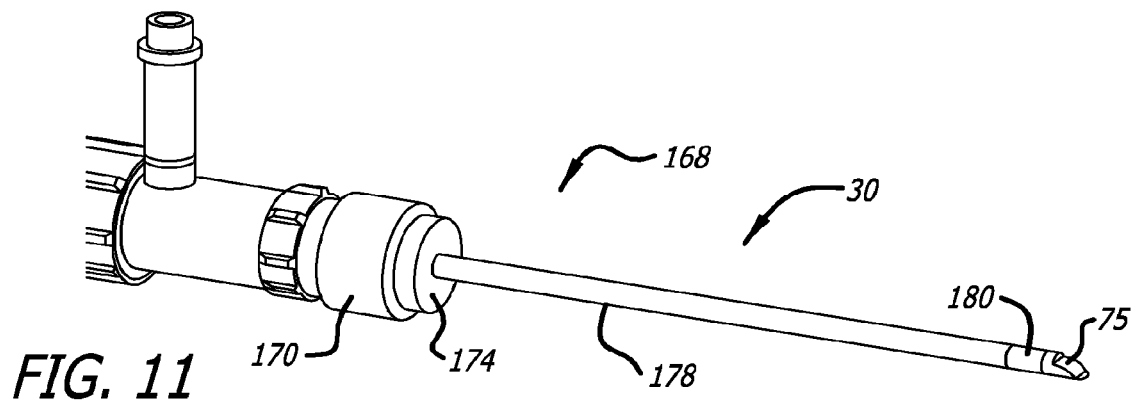
FIGS. 11 and 12 depict a washing system disposed over a swing prism endoscope in a resting state.
Figure 12:
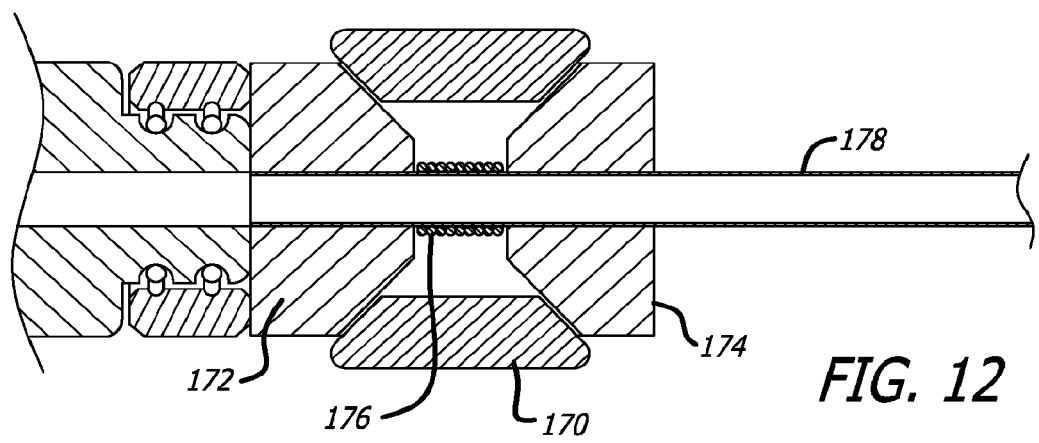
Figure 13:
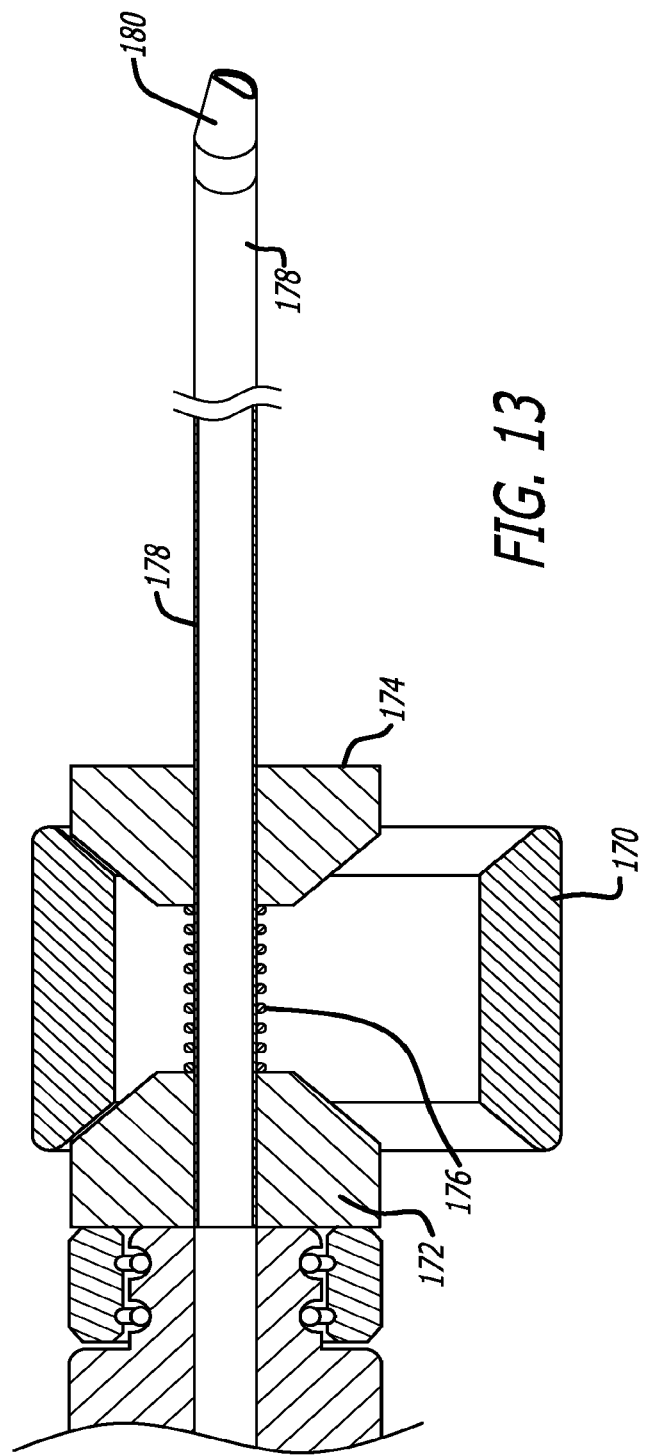
FIG. 13 depicts the washing system shown in FIGS. 11 and 12 in a forward position or activated state.

A washing system 168 is shown disposed on the endoscope 10 in FIGS. 11 through 13. The washing system includes a button 170 positioned between first and second cones 172 and 174. The first and second cones 172, 174 are connected together by a spring 176 (FIG. 12). In this embodiment, the first cone 172 is fixed to the endoscope and the second cone 174 is connected to a wiping sheath 178. A distal end of the wiping sheath includes a cloth 180, which may be a hydrophilic elastomer. As shown in FIGS. 11 and 12, the washing system 168 is in its resting state, with the extension spring 176 in a drawn state and the first and second cones at a minimum distance from one another. In the resting state, the cloth 180 is positioned proximal to the lens 75 of the endoscope as shown in FIG. 11.

To move the washing system 168 forward to clean the lens 75 of the endoscope, the button 170 is pushed, such that it moves off the central axis of the endoscope in any direction. This movement of the button causes the second cone 174 to move forward since the first cone 172 is fixed to the endoscope. Driving the second cone 174 forward or in the distal direction causes the wiping sheath 178 to also move forward and push the cloth 180 over the lens 75 since it is attached to the second cone. The activated state of the washing system is shown in FIG. 13. The cloth 180 is elastomeric, and therefore, it conforms to the shape of the lens 75 and wipes any debris, mucus, and/or blood off of the lens. The porous hydrophilic cloth also absorbs any fluid which has collected on the lens. Once the button 170 is released, the spring recoils and draws the cloth back over the lens into a position proximal to the lens.

In one embodiment, the cloth 180 may have a supporting structure, such as, rods, mesh, or the like, to prevent the cloth from bunching or folding up when the cloth is pushed forward in the distal direction. Also, it has been contemplated that the leading distal edge of the cloth 180 may be silicone, rubber or some other hydrophilic material to wipe the fluid forward (distally) from the lens 75. The leading distal edge of the cloth may also have multiple slits cut into it to help wipe or push debris off of the lens.

Figure 14:
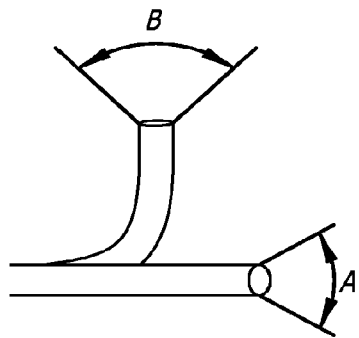
FIG. 14 depicts viewing angles of a typical endoscope having a flexible or steerable shaft.
Figure 15:
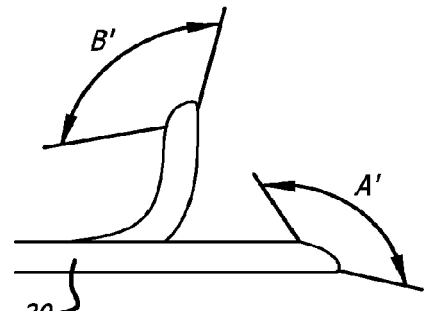
FIG. 15 depicts viewing angles of a swing prism endoscope having a flexible or steerable shaft.

In the embodiment described above, the endoscope 10 may have a relatively rigid shaft. However, it has been contemplated that the shaft of the endoscope 10 may also be flexible to greatly enhance the viewing area of the endoscope. As shown in FIG. 14, a typical endoscope is shown that can visualize a fixed area A or B at any position within the flexible range of the typical endoscope. One embodiment of the current invention, shown in FIG. 15, can visualize a much larger range A' or B' by modifying the flex or position of the swing prism within the endoscope 10. It is contemplated that a flexible endoscope can be constructed with fiber scope or video chip technology. Such flexible endoscope may be useful for intra nasal, intra sinus, skull bass, laryngeal, orthopaedic, abdominal and other surgeries where a variable and large viewing range is desired.

In one embodiment, the endoscope 10 uses rod lens technology to acquire and transfer images along the shaft of the endoscope. In another embodiment, video chip technology as understood in the art requires rigidity around the distal portion of the endoscope and the images are transferred over a wire that enables the shaft of the endoscope to be downsized. Acquisition of the image via video chip technology may also allow the diameter of the distal portion of the endoscope to be downsized, without compromising the quality of the image or the size of the image that is viewed by the user. Current video chip technology requires the distal end of the endoscope to have a minimum diameter of about 1.2 mm to about 1.8 mm. With the addition of illumination fibers and mechanics for the swing prism, an endoscope using video chip technology may be constructed with a diameter at the distal portion of the endoscope of less than 4 mm.

Figure 16:
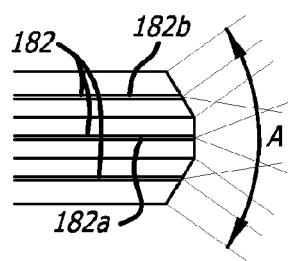
FIG. 16 depicts a reduced number of optical fibers that lapped at various angles to create a wider illuminating field.

Certain embodiments are disclosed herein that increase the field of illumination and increase the field of image capture after miniaturizing an endoscope, such as the swing prism endoscope. When an endoscope is reduced in size or miniaturized, the number of optical fibers is decreased, thereby reducing the field of illumination utilizing such optical fibers. Also, miniaturizing an endoscope reduces the field of image capture due to the smaller size of optical components for the return image. As shown in FIG. 16, one embodiment of a miniaturized endoscope includes optical fibers 182 lapped at various angles from about 0 degrees to about 30 degrees. In this embodiment, the optical fibers can be arranged with such angles increasing from a chosen interior fiber 182a to the outer or edge fibers 182b, and thereby, creating a wider illuminating field A.

Figure 17:
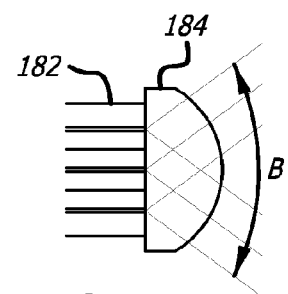
FIG. 17 depicts a divergent lens positioned at a distal end of optical fibers to create a wider illuminating beam.

In another embodiment shown in FIG. 17, a diverging lens 184 can be disposed at the end of the optical fibers 182 to create a wider illuminating beam B. In this embodiment, the optical fibers are lapped at about 0 degrees; however, the diverging lens can be combined with lapped optical fibers similar to those shown in FIG. 16 to amplify the divergence of the illuminating beam. The diverging or expansion lens can be fabricated from a block of glass with the required curvature for beam divergence and then parted by using a saw or high pressure water jet to minimize edge defects. The non-functional sides of the individual diverging lens could be coated with nickel or gold to reduce optical leakage by creating internally reflective surfaces. It is noted that the input power to the optical fibers of a miniaturized endoscope can be increased to match the illumination intensity of a standard endoscope.

Figure 18:
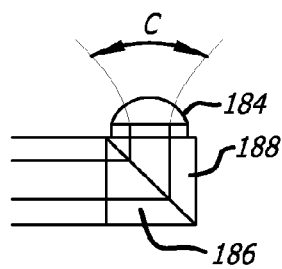
FIG. 18 depicts a partial view of a miniaturized endoscope having first and second prisms and a divergent lens to increase the field of view.
Figure 19:
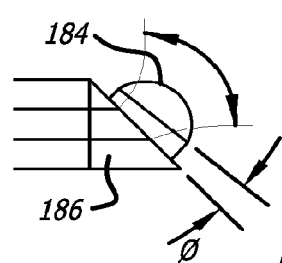
FIG. 19 depicts a partial view of a miniaturized endoscope having a first prism and a divergent lens to increase the field of view.

To maintain or improve the field of view captured by a return beam through a prism, a divergent lens may be used on a miniaturized endoscope. As shown in FIG. 18, the miniaturized endoscope includes a first prism 186 and a second prism 188 contacting the first prism. There is also a divergent lens 184 disposed on the second prism 188 which increases the field of view C. FIG. 19 shows a miniaturized endoscope with only the first prism 186 being used and the divergent lens 184 disposed near the first prism. As shown in FIG. 19, Ø may be optimized for the return beam relative to the axis of the endoscope.

Figure 20:
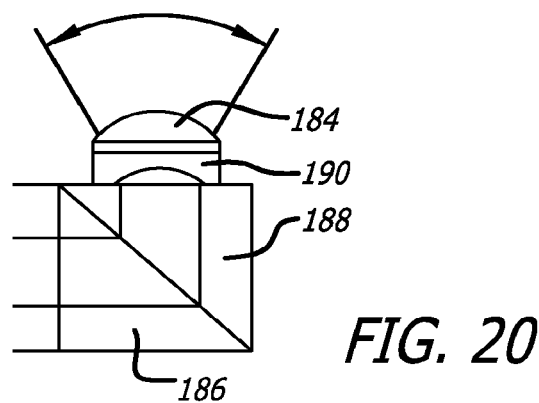
FIG. 20 depicts a partial view of a miniaturized endoscope having first and second prisms and using a divergent lens in combination with a concave lens to increase the field of return image capture.

In another embodiment, a concave or negative refractive power lens may be mounted to the distal prism 186 to increase the field of return image capture for the return optics. As shown in FIG. 20, a negative refractive power lens or concave lens 190 is used in combination with the positive refractive power lens or divergent lens 184 to achieve a wider angle of image capture while minimizing aberrations on the fiber optics to increase image quality. In this embodiment, the steering mechanism for the prism may be eliminated if the range of the wide angle image is sufficient to cover the target area without steering the prism. In embodiments where the steering mechanism is eliminated, this will create more space within the miniaturized endoscope for adding more illuminating fiber optics to better illuminate the target area and improve reliability.

Figure 21:
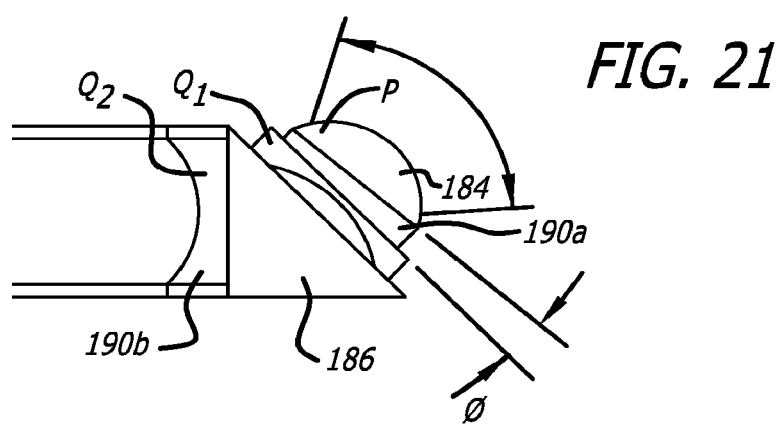
FIG. 21 depicts a partial view of a miniaturized endoscope having a first prism and using a divergent lens in combination with two concave lenses to increase the field of return image capture.

In another embodiment shown in FIG. 21, two negative refractive power lenses are used with a single prism of a miniaturized endoscope including a prism steering mechanism. As shown in FIG. 21, a first negative refractive power lens or concave lens 190a is disposed distally of the prism 186 and a second negative refractive power lens or concave lens 190b is disposed proximally of the prism 186. In this embodiment, the first and second concave lenses can operate in conjunction with one another or individually as required. Also, the positive refractive power lens or divergent lens 184 is positioned distally of the first concave lens 190a. The divergent lens 184 works with the first and second concave lenses 190a and 190b to reduce optical aberrations in the lens system and to enhance the image quality.

Figure 22A:
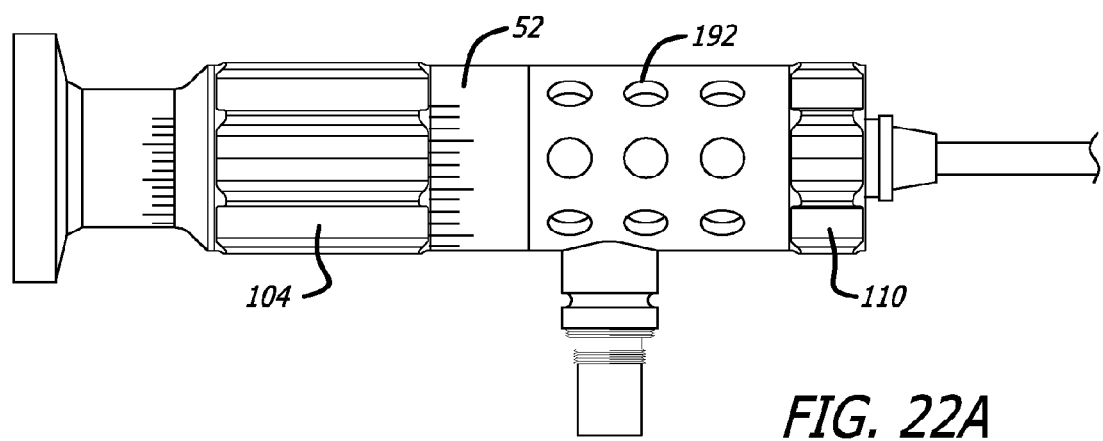
FIG. 22A depicts an embodiment of an endoscope having a handle with an open configuration.

Referring now to FIG. 22A, one embodiment of the handle 52 of the endoscope may be open to allow fluid to freely move in and out of the handle 52. In this way, the handle 52 of the endoscope may be cleaned and dried while the sealed chamber 151 remains sealed. In one embodiment the proximal body 52 has an open configuration by drilling holes 192 into the housing of the handle 52. In another embodiment, a mesh may be used to create an open handle 52. Without an open configuration, there is a possibility that fluid may leak into the inner chamber of the handle 52 through a broken seal. Any fluid that enters the inner chamber of the handle 52 has the potential of rusting components and allowing bacterial growth. Therefore, providing the handle 52 with an open configuration prevents this problem in the inner chamber of the handle because any fluid entering will more easily evaporate or be drained through the holes 192.

Light fiber 194 extends from the light post 193 and into the sealed chamber 151 or optical chamber. In this embodiment, the light fiber must be free moving in order to allow the endoscope shaft to rotate in relation to the light post. In order to maintain the seal on the sealed chamber 151, a flexible sheath 196 covers the light fiber 194 and is affixed to the sealed chamber. This flexible sheath may be formed of silicone or steel. The flexible sheath 196 allows the light fiber to move and the flexible sheath protects the light fiber from damage.

Figure 22B:
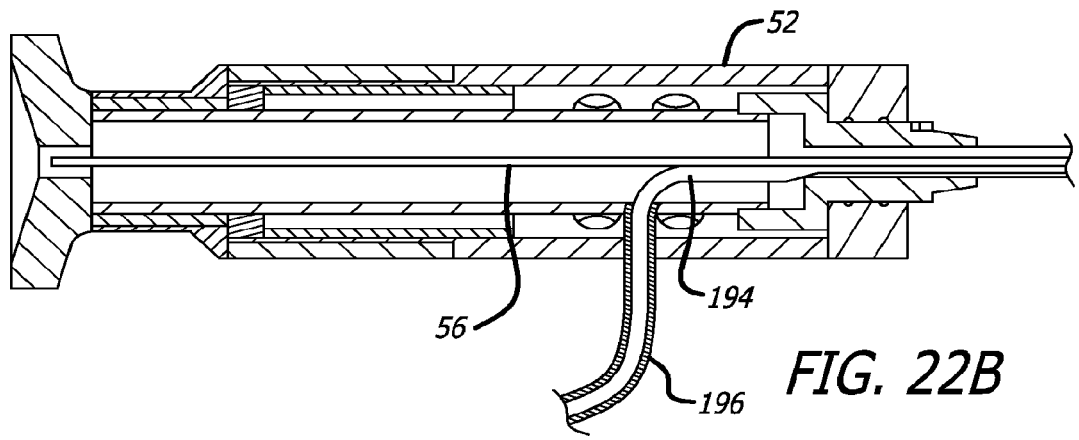
FIG. 22B depicts an embodiment of an endoscope without a light post on a handle.

In another embodiment shown in FIG. 22B, the light post has been removed, and the light fiber 194 within the flexible sheath 196 exits the handle 52. In this embodiment, the light fiber would be connected to a light cable further away from the endoscope. Removing the light post prevents heat build up on the handle where the user holds the endoscope.

Figure 23:
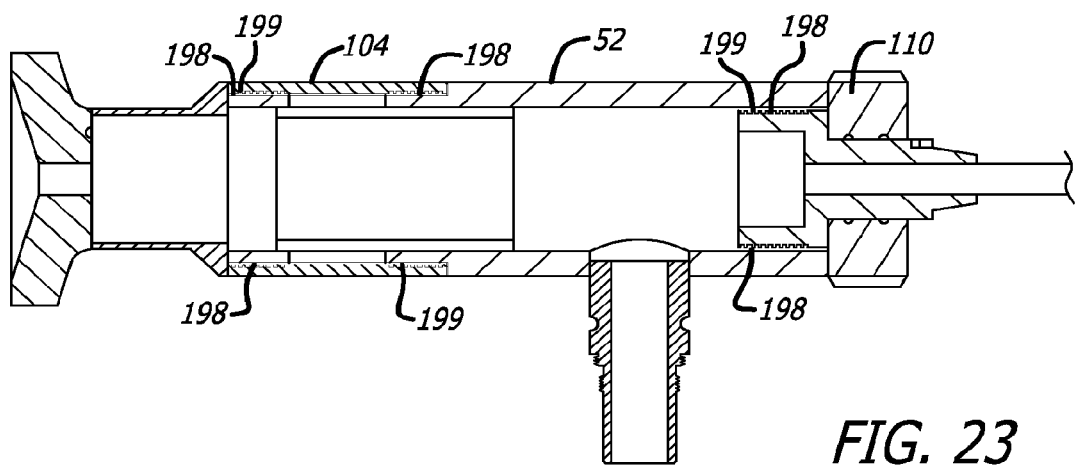
FIG. 23 depicts a cross-sectional view of handle of an endoscope that includes ferric fluid seals.

Yet another embodiment of an endoscope is shown in FIG. 23, where the internal mechanisms of the endoscope are sealed from the outside environment. FIG. 23 shows a cross-sectional view of the handle 52 of the endoscope 10 with the internal driving mechanisms removed for clarity. In this embodiment, ferric fluid, which can be an oil containing iron particles mixed within, is injected into spaces 198 between the dials or dials 104 and 110 and the inside portion of the handle 52. Teeth 199 are formed on the surfaces of the dials 104 and 110 to trap the ferric fluid as shown in FIG. 23. It has also been contemplated that teeth can be formed on the internal surface of the handle. Either the dials 104 and 110 or the handle 52 can contain a magnet disposed near or forming spaces 198, and these magnets can attract and bond with the magnetic ferric fluid. In another embodiment, both the dials and the handle may contain magnets at the spaces 198. As shown in FIG. 23, the teeth on the distal dial 110 are formed on a proximal portion of the dial that is connected with the shaft of the endoscope and positioned within the internal chamber of the handle. Therefore, the spaces formed around the internal circumference of the handle become a fluid seal.

This bonding between the magnets within the dials 104 and 110 or the handle 52 and the ferric fluid allows the dials to move in relation to the handle with little or no friction. Also, this bonding seals the internal chamber of the handle from the outside environment. These fluidic seals will not wear like a typical O-ring and they are capable of withstanding high pressures.

Figure 24A:
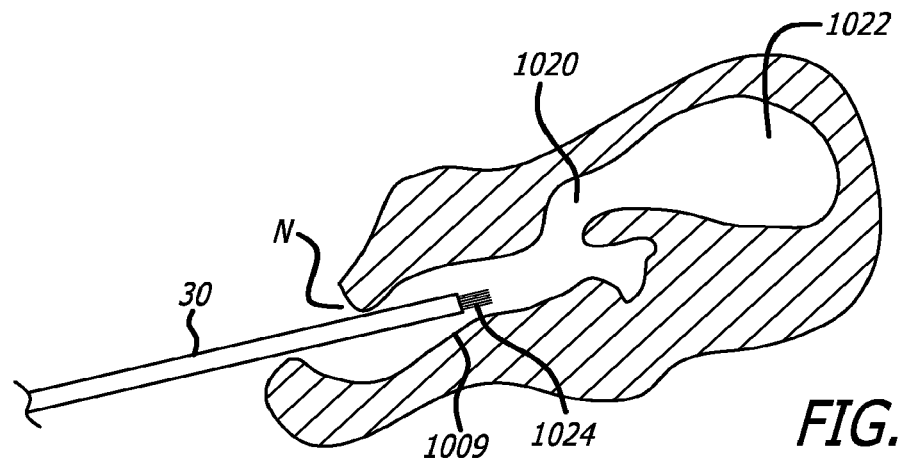
FIG. 24A depicts a swing prism endoscope introduced into a nostril of a human or animal subject, according to one embodiment of the present invention.
Figure 24B:
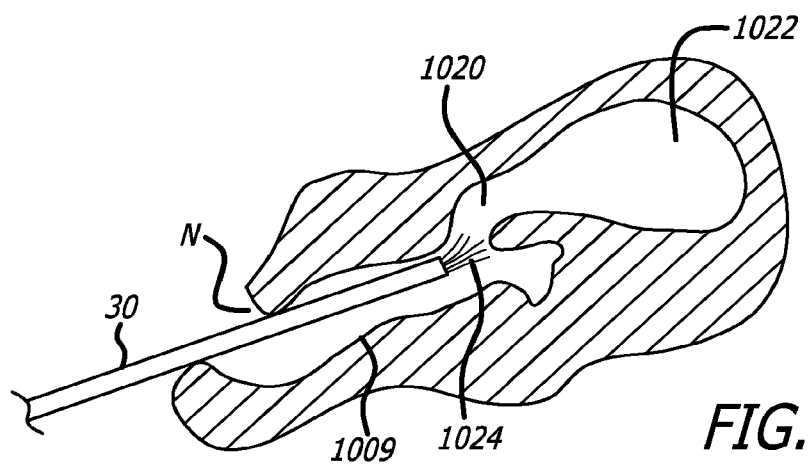
FIG. 24B depicts the endoscope of FIG. 24A advanced farther into the paranasal anatomy, with the swing prism adjusted to view at an angle relative to the longitudinal axis of the swing prism scope.

Referring now to FIGS. 24A and 24B, one embodiment of a method of using a swing prism endoscope in the nasal and paranasal anatomy is described. For ease of illustration, FIGS. 24A and 24B show a nostril N, a nasal cavity 1009, and a non-specific paranasal sinus 1022 with a natural paranasal sinus ostium 1020. In various embodiments, the endoscope 10 may be used in procedures addressing the maxillary, frontal, sphenoid and/or ethmoid paranasal sinuses and their related ostia. FIGS. 25A-25D, for example, show a method involving dilation of a natural ostium of a sphenoid sinus. However, it may be even more advantageous to use a swing prism endoscope of the present application in a procedure involving the maxillary and/or frontal paranasal sinuses, as the natural openings into these sinuses are usually difficult to visualize using an endoscope without removing one or more natural anatomical structures. Therefore, although FIGS. 24A and 24B show a generic paranasal sinus, and FIGS. 25A-25D show a sphenoid sinus, the endoscopes of the present invention may be used in any suitable procedure involving any paranasal sinus and/or nasal cavity. In further alternative embodiments, endoscopes of the present application may be used in procedures involving other portions of ear, nose or throat anatomy, such as but not limited to Eustachian tube procedures such as dilation and/or stent placement, repair of cranio-facial fractures, airway procedures such as subglottic stenosis dilation, tonsillectomy, adenoidectomy and/or the like.

As shown in FIG. 24A, in one embodiment a swing prism endoscope 10 may be inserted into a nostril N of a human or animal subject with the viewing angle of the scope adjusted to approximately 0 degrees (i.e., a straight ahead view), as demonstrated by the ray lines 1024. In alternative embodiments, the endoscope 10 may not be capable of viewing at 0 degrees but may be capable of between about 5 degrees and about 10 degrees as the most "straight ahead" angle. In either case, the physician may advance the endoscope 10 through the nasal cavity 1009 using the straight ahead view, moving toward, for example, a paranasal sinus ostium 1020, such as an ostium of a maxillary, frontal, sphenoid or ethmoid sinus. FIG. 24B shows endoscope 10 in a more advanced location. At some point during or after advancing endoscope 10, the physician may adjust the swing prism of scope 30 to change its viewing angle, for example to look in the direction of ostium 1020. In one embodiment, endoscope 10 includes an automatic focusing element, so that as the swing prism is adjusted and the viewing angle changed, endoscope 10 automatically refocuses. After viewing ostium 1020, the physician may decide to leave the viewing angle the same or make further adjustments to view different anatomy, an additional device inserted into the paranasal anatomy, and/or the like. In some embodiments, at any point during a procedure, a physician may be able to lock the viewing angle of endoscope 10 at a desired angle. When withdrawing the device from the human or animal subject's nostril, the physician may again adjust the swing prism viewing angle back to 0 degrees or may leave the angle as it was during any part of the procedure. Such a method, or any of a number of variations thereof, allows a physician to view anatomy of a nasal cavity 1009, paranasal sinus ostium 1020 and/or paranasal sinus 1022, as well as one or more surgical devices, during a procedure without having to switch out multiple different endoscopes or to remove tissue to look around corners.

Figure 25A:
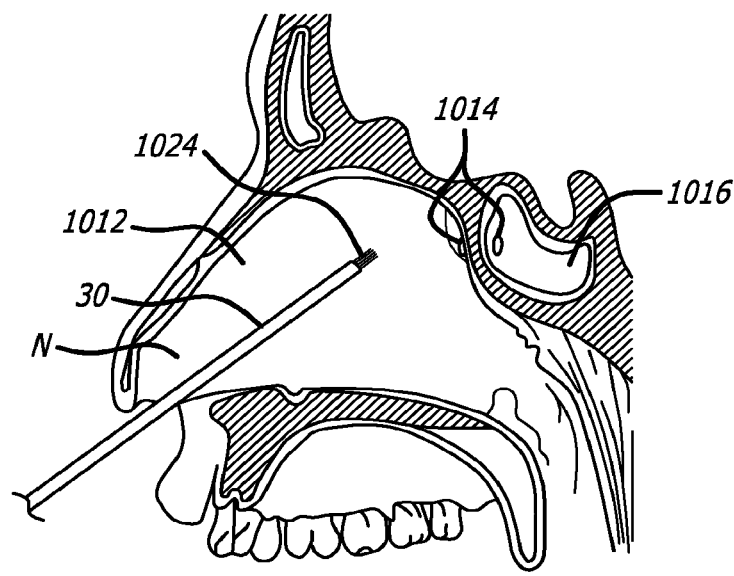
FIG. 25A-25D depict partial sagittal sectional views through a human head showing various steps of a method of using a swing prism scope to view and facilitate accessing a paranasal sinus using a sinus guide, according to one embodiment of the present invention.

FIGS. 25A through 25D are illustrations of partial sagittal sectional views through a human head showing various steps of a method for viewing and treating an ostium of a paranasal sinus, which in this example is a sphenoid sinus. In FIG. 25A, the swing prism endoscope 10 is introduced through a N nostril and through a nasal cavity 1012 to a location close to an ostium 1014 of a sphenoid sinus 1016. The endoscope is used to view surrounding anatomy using a first, straight ahead viewing angle (or approximately straight ahead, such as between about 5 degrees and about 10 degrees angled from the endoscope longitudinal axis).

Figure 25B:
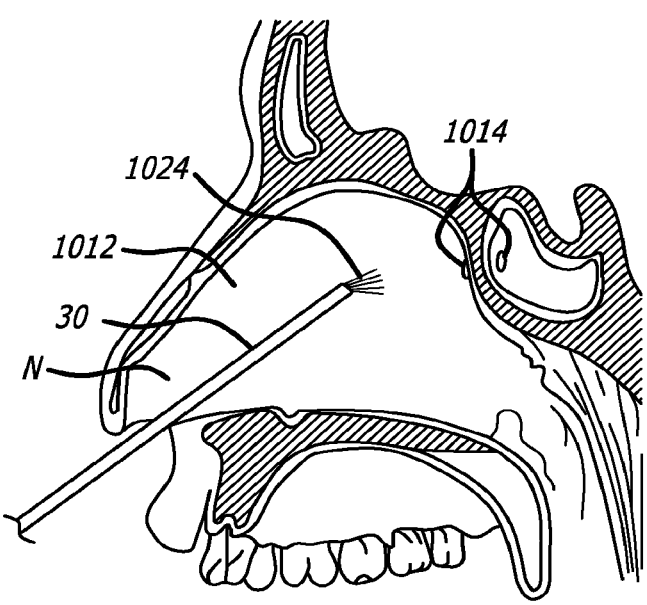

In FIG. 25B, the angle of view of the endoscope 10 is altered to view an ostium 1014 of a sinus 1016. In an alternative embodiment, one or more therapeutic or diagnostic devices may be advanced into the nasal cavity 1012 before the angle of view of the endoscope 10 is adjusted. In fact, the endoscope 10 may generally be advanced, adjusted, removed and the like in conjunction with any additional device(s) in any suitable order or manner as desired.

Figure 25C:
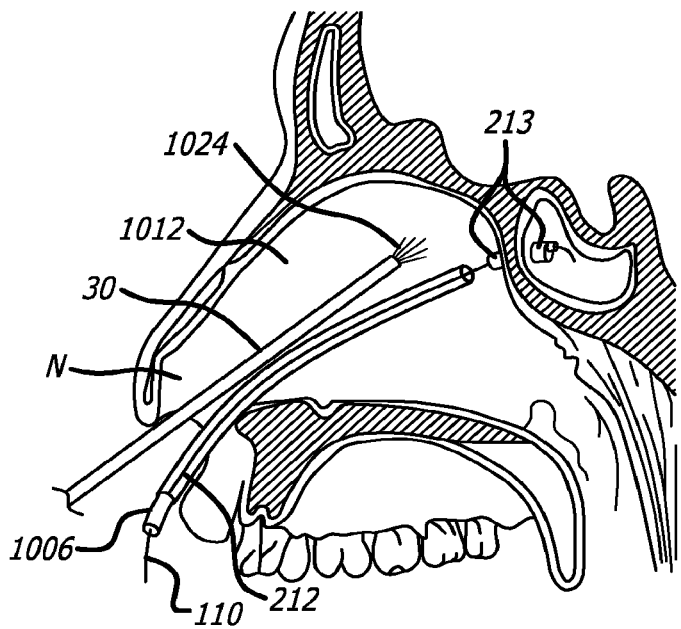

As shown in FIG. 25C, in one embodiment, a guide catheter 212 may next be advanced into the nasal cavity 1012, in some cases but not necessarily preloaded with a guidewire 110 and/or a balloon catheter. The guidewire 110 may then be advanced out of the distal end of the guide catheter 212 such that it passes through the sinus ostium 1014 and into the sphenoid sinus 1016. A working device 1006, such as a balloon catheter, can be introduced over the guidewire 110, through the guide catheter, to position an expandable member 213 such as an inflatable balloon, into the sinus ostium 1014.

Figure 25D:
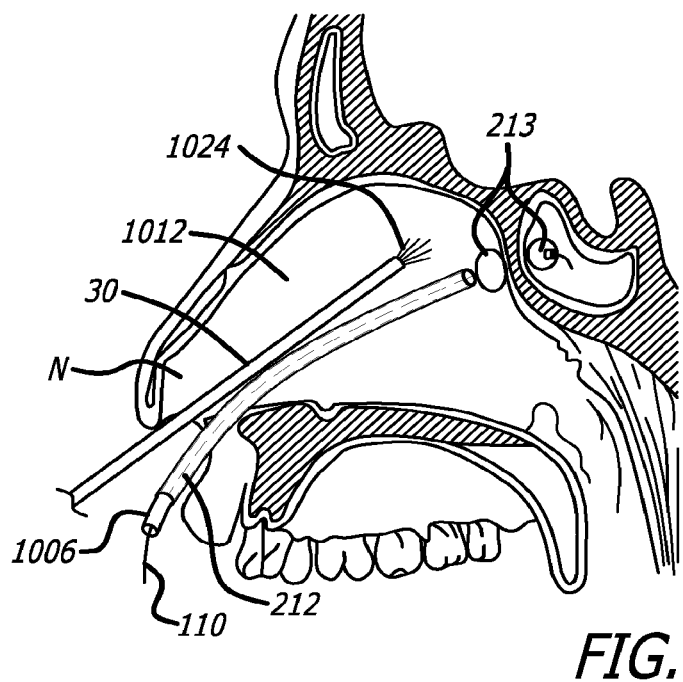

Thereafter, as shown in FIG. 25D, working device 1006 is used to perform a diagnostic or therapeutic procedure. In this particular example, the procedure is dilation of the sphenoid sinus ostium 1014, where the balloon of device 1006 is expanded to enlarge the ostium 1014. After completion of the procedure, the sinus guide catheter 212, guidewire 110 and working device 1006 are withdrawn and removed. The entire procedure can be observed using the swing prism endoscope 10.

The features of the present disclosure may also be used to dilate or modify any sinus ostium or other man-made or naturally occurring anatomical opening or passageway within the nose, paranasal sinuses, nasopharynx or adjacent areas. In this or any of the procedures described in this patent application, the operator may additionally advance other types of catheters, and guidewire 110, guide catheter 212 or both may be steerable (e.g. torquable, actively deformable) or shapeable or malleable. Additionally, in various alternative embodiments, the endoscope 10 and one or more other devices, such as a guide catheter 212, may be integrated. In one embodiment, for example, a guide catheter 212 may include an endoscope lumen through which the endoscope 10 may pass.

The scope 30 may be useful to reduce or eliminate the need for fluoroscopic visualization during placement of a sinus guide and/or for visualization of the procedure performed by working device 1006. Being configured with a swing prism providing a one hundred sixty five degree viewing field, it can provide the capability to see an opening into a paranasal sinus and possibly even inside the sinus itself, and thus the endoscope may provide sufficient visual feedback for use in guiding guidewire 110 into the desired sinus.

Figure 26:
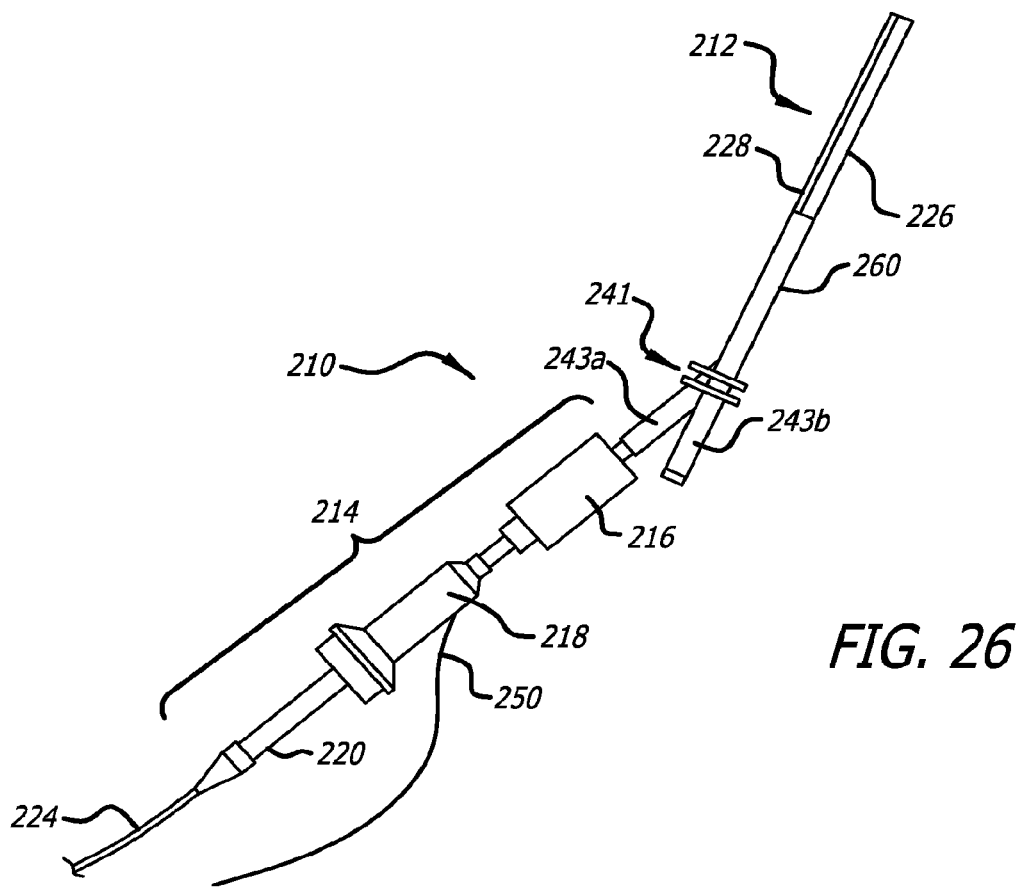
FIG. 26 depicts a perspective view of one embodiment of a guide system.

FIG. 26 shows one embodiment of a sinus guide system 210 which can be used with the swing prism endoscope 10 of the present disclosure. Sinus guide 212 may be straight, malleable, or it may incorporate one or more preformed curves or bends as further described above, as well as in U.S. Patent Publication Nos. 2006/004323; 2006/0063973; and 2006/0095066, for example, each of which are incorporated herein, in their entireties, by reference thereto. In embodiments where sinus guide 212 is curved or bent, the deflection angle of the curve or bend may be in the range of up to about 135 degrees. This sinus guide system 210 comprises a sinus guide 212 and a camera/transmission/endoscope assembly 214. This embodiment of the sinus guide 212 is shown in more detail in FIGS. 28A-28C. As shown, this sinus guide 212 comprises a sinus guide body 226 and an endoscope channel 228 in generally side-by-side arrangement. As previously described, the swing prism endoscope 10 may be inserted separately from the sinus guide system 210. In certain applications, however, the endoscope 10 also can be inserted through the endoscope channel 228. Accordingly, the system 210 can also lack an endoscope channel 228. In either approach, the swing prism endoscope can be connected to a camera/transmission assembly and to a console 234 including a monitor 236 and video recorder 240.

The sinus guide body 226 can embody a tube 244 having a lumen 245 (e.g., see FIG. 28B), such as a polymer tube made of biocompatible polymeric material. Optionally, a liner 246 (FIG. 28B) may be disposed within the lumen 245 of the tube 244. Such liner may be formed of lubricious or smooth material such as polytetrafluoroethylene (PTFE). Also, optionally, a proximal portion of the tube 244 may be surrounded by an outer tube member 242 formed of material such as stainless steel hypotube. In the embodiment shown, a distal portion of the tube 244 extends out of and beyond the distal end of outer tube 242. This protruding distal portion of the tube 244 may be straight or curved. Also, it may be pre-formed at the time of manufacture or malleable to a desired shape at the time of use. When intended for use in accessing the ostium of a paranasal sinus, the distal portion of tube 244 may be curved to form an angle A from about 0 degrees to about 120 degrees. For example, a series of sinus guides 212 having angles A of 0, 30, 70, 90 and 110 degrees may be provided thereby allowing the physician to select the sinus guide angle A that is most appropriate for the particular paranasal sinus ostium to be accessed.

Figure 28A:
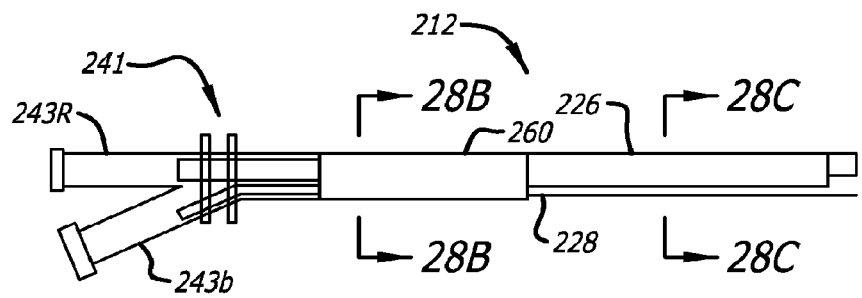
FIG. 28A depicts a side view of the guide catheter of the system of FIG. 26.
Figure 28B:
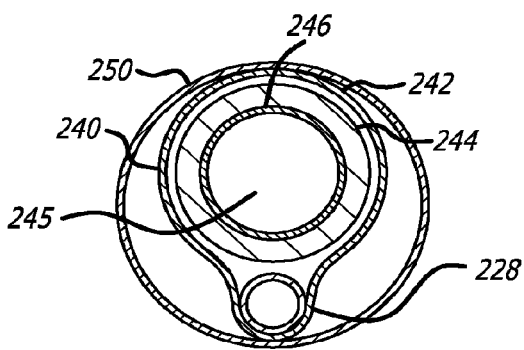
FIG. 28B depicts a cross sectional view through line 28B-28B of FIG. 28A.
Figure 28C:
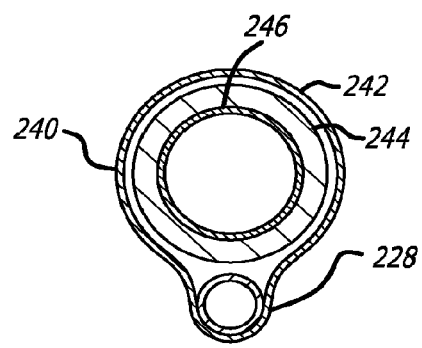
FIG. 28C depicts a cross sectional view through line 28C-28C of FIG. 28A.

Additionally, in some embodiments, a rotation grip 260 may be positioned about a proximal portion of the sinus guide 210, as seen in FIGS. 26, 28A and 28B. This rotation grip 260 may have a smooth or textured round outer surface (e.g., it may be a cylindrical tube) that may be grasped between the fingers of the operator's hand and easily rotated, thereby facilitating rotation (e.g., rolling) of the sinus guide 212 as it is being used. Such rotation of the sinus guide 212 may be desirable for a number of reasons including but not limited to positioning of the distal end of the sinus guide 212 at a desired location.

In the event it is desirable to configure the sinus guide system with an endoscope channel, it is contemplated that the channel 228 may comprise any structure (e.g., tube, track, groove, rail, etc.) capable of guiding the advancement of a flexible endoscope. In the particular examples shown in these figures, the endoscope channel 228 comprises a tube (e.g., a polymer tube) having a lumen 229 extending therethrough. In the embodiment seen in FIGS. 26-28C, the endoscope channel 228 is attached to and extends along substantially the entire length of the sinus guide body 226. In another embodiment, the endoscope channel 228 can be inside the sinus guide body 226. In other embodiments, the endoscope channel 228 may be interrupted, non-continuous or may extend over less than the entire length of the sinus guide body 226. An outer skin 240 may be heat shrunk or otherwise disposed around the sinus guide body 226 and endoscope channel 228 to hold the endoscope channel 228 at a desired position on the outer surface of the sinus guide body 226. Alternatively, the endoscope channel 228 may be attached to the sinus guide body 226 at one or more locations by any other suitable attachment substance, apparatus or technique, including but not limited to adhesive, soldering, welding, heat fusion, coextrusion, banding, clipping, etc. The particular circumferential location of the endoscope channel 228 can be important in some applications, particularly when the sinus guide body 226 includes a curve formed in its distal portion 244. In this regard, for some applications, the endoscope channel 228 may be affixed at a particular circumferential location on the sinus guide body 226 to allow an endoscope 10 inserted through the endoscope channel 228 to provide a view from a desired or optimal vantage point, without obstruction from adjacent anatomical structures. It is also to be recognized that a second endoscope (not shown) distinct from the above described swing prism endoscope and which incorporates a swing prism or otherwise defines flexible structure can be inserted through the endoscope channel.

Again referring to FIGS. 26-28C, a proximal Y connector 241 may be attached to the proximal end of the sinus guide 212. A first arm 243b of this Y connector comprises a female Luer fitting that is connected to the lumen 245 of the sinus guide body 226. The other arm 243a is a female Luer fitting that is connected to the lumen 229 of the endoscope channel 226.

Figure 27:
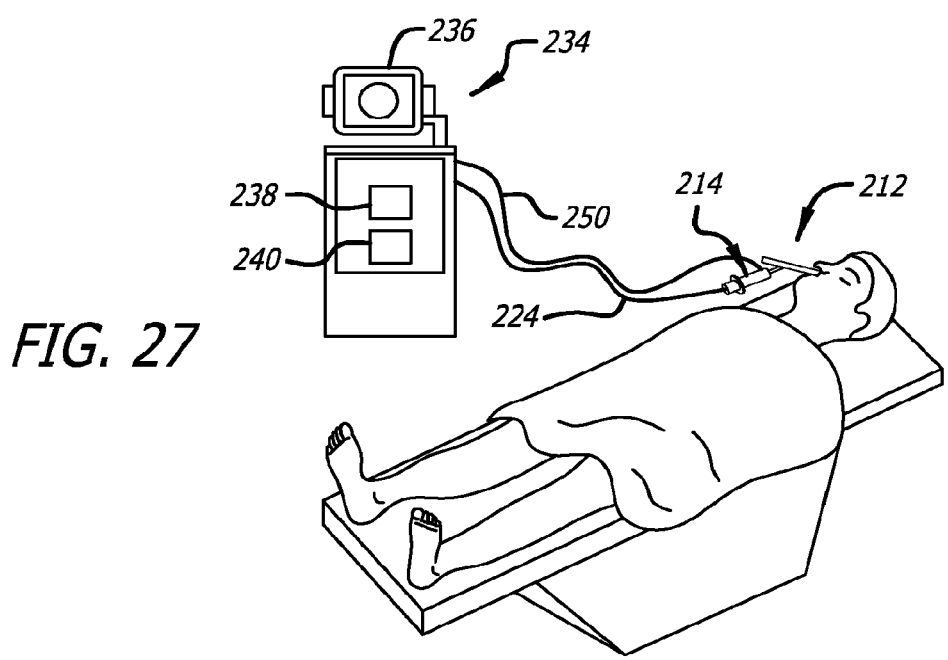
FIG. 27 depicts a perspective view of the guide system in use on a human subject.
Figure 29:
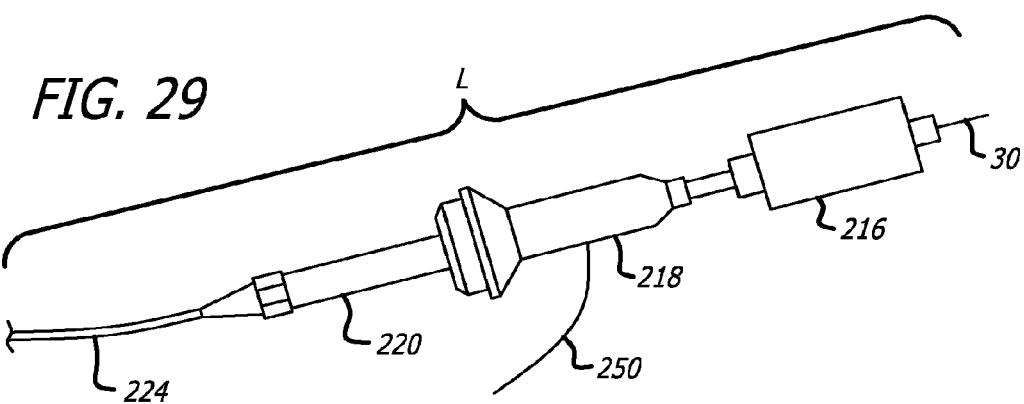
FIG. 29 depicts a side view of the connector/camera/light cable assembly of the system of FIG. 26.

A camera/cable/endoscope assembly 214 is attachable to arm 243a. In the particular embodiment shown in FIGS. 26 and 29, the camera/cable/endoscope assembly 214 comprises an adjustable scope/lock extension 216, a camera 220 and a monitor cable 224. The scope body 30 can be advanced through the scope/lock extension 216 and through the lumen 229 of the endoscope channel 228. As shown in FIG. 27, the light cable 250 and monitor cable 224 may be connected to console 234 that houses a monitor 236, light source 238 and video recorder 240. Alternatively, the endoscope 10 can be directly connected to a console 234 separate from the sinus guide system 212.

The invention has been described hereabove with reference to certain examples or embodiments of the invention, but various additions, deletions, alterations and modifications may be made to these examples and embodiments and or equivalents may be substituted without departing from the intended spirit and scope of the invention. For example, any element or attribute of one embodiment or example may be incorporated into or used with another embodiment or example, unless to do so would render the embodiment or example unsuitable for its intended use. In addition, many modifications may be made to adapt a particular situation, material, composition of matter, process, process step or steps, to the objective, spirit and scope of the present invention. All such modifications are intended to be within the scope of the claims appended hereto.

What is claimed:

1. An endoscope configured to pass into a head of a human or animal subject, the endoscope comprising:
    (a) a handle, wherein the handle comprises a rotatable user input feature;
    (b) an elongate tubular member extending distally from the handle, wherein the tubular member comprises a proximal end and a distal end, wherein the tubular member defines a hollow tubular interior extending the length of the tubular member, wherein the tubular member further defines a central longitudinal axis;
    (c) a viewing window disposed at the distal end of the tubular member;
    (d) a pivotable prism disposed within the hollow tubular interior of the tubular member proximal to the distal end of the tubular member, wherein the pivotable prism comprises a plurality of teeth, wherein the pivotable prism is configured to change a direction of view of the endoscope, wherein the user input feature is operable to adjust a viewing angle of the endoscope by pivoting the pivotable prism within the hollow tubular interior; and
    (e) a threaded shaft comprising a threaded portion, wherein the threaded shaft is rotatably disposed within the tubular member about a second longitudinal axis, wherein the second longitudinal axis is parallel to the central longitudinal axis, wherein the threaded portion is configured to engage the teeth of the pivotable prism, wherein the threaded shaft is configured to rotate about the second longitudinal axis within the tubular member in response to rotation of the user input feature to cause pivoting of the pivotable prism about a third axis, wherein the third axis is perpendicular to a plane bisecting the elongate tubular member, wherein the plane is parallel to the central longitudinal axis.

2. The endoscope of claim 1, wherein the second longitudinal axis does not pass through the pivotable prism.

3. The endoscope of claim 1, wherein the third axis passes through the pivotable prism.

4. The endoscope of claim 1, wherein the pivotable prism is disposed within the length of the tubular member defining the viewing window.

5. The endoscope of claim 1, further comprising a lens disposed in the elongate shaft.

6. The endoscope of claim 1, wherein the viewing angle ranges from between about 0 degrees to about 120 degrees.

7. An endoscope configured to pass into a head of a human or animal subject, the endoscope comprising:
    (a) a handle, wherein the handle comprises a rotatable user input feature;
    (b) an elongate tubular member extending distally from the handle, wherein the tubular member comprises a proximal end and a distal end, wherein the tubular member defines a hollow tubular interior extending the length of the tubular member, wherein the tubular member further defines a central longitudinal axis;
    (c) a viewing window disposed at the distal end of the tubular member;

(d) a pivotable prism disposed within the hollow tubular interior of the tubular member proximal to the distal end of the tubular member and within the length of the tubular member defining the viewing window, wherein the pivotable prism comprises a plurality of teeth, wherein the pivotable prism is configured to change a direction of view of the endoscope, wherein the user input feature is operable to adjust a viewing angle of the endoscope by pivoting the pivotable prism within the hollow tubular interior about a prism axis; and (e) a threaded shaft comprising a worm threaded portion, wherein the threaded shaft is rotatably disposed within the tubular member about a second longitudinal axis, wherein the second longitudinal axis is parallel to the central longitudinal axis, wherein the worm threaded portion is configured to engage the teeth of the pivotable prism, wherein the threaded shaft is configured to rotate about a second longitudinal axis within the tubular member to cause pivoting of the pivotable prism about the prism axis in response to rotation of the user input feature, wherein the prism axis is perpendicular to a plane bisecting the elongate tubular member, wherein the plane is parallel to the central longitudinal axis.

* * * * *